US011911349B2

(12) United States Patent
Chlopicki et al.

(10) Patent No.: US 11,911,349 B2
(45) Date of Patent: *Feb. 27, 2024

(54) RAPIDLY IMPROVING VASCULAR CONDITIONS BY ADMINISTERING VITAMIN K

(71) Applicant: NATTOPHARMA AS, Oslo (NO)

(72) Inventors: Stefan Chlopicki, Cracow (PL); Katarzyna Maresz, Cracow (PL); Anna Bar, Przemysl (PL)

(73) Assignee: NATTOPHARMA AS, Oslo (NO)

( * ) Notice: Subject to any disclaimer, the term of this patent is extended or adjusted under 35 U.S.C. 154(b) by 0 days.

This patent is subject to a terminal disclaimer.

(21) Appl. No.: 16/372,173

(22) Filed: Apr. 1, 2019

(65) Prior Publication Data

US 2019/0328683 A1 Oct. 31, 2019

Related U.S. Application Data

(60) Provisional application No. 62/816,499, filed on Mar. 11, 2019, provisional application No. 62/650,674, filed on Mar. 30, 2018.

(51) Int. Cl.
| | | |
|---|---|---|
| A61K 31/122 | (2006.01) | |
| A61P 9/10 | (2006.01) | |
| A61P 9/14 | (2006.01) | |
| A61K 31/592 | (2006.01) | |
| A61K 31/593 | (2006.01) | |
| A61K 45/06 | (2006.01) | |

(52) U.S. Cl.
CPC .......... *A61K 31/122* (2013.01); *A61K 31/592* (2013.01); *A61K 31/593* (2013.01); *A61P 9/10* (2018.01); *A61P 9/14* (2018.01); *A61K 45/06* (2013.01)

(58) Field of Classification Search
CPC .. A61K 31/122; A61K 31/592; A61K 31/593; A61P 9/10; A61P 9/14
See application file for complete search history.

(56) References Cited

U.S. PATENT DOCUMENTS

| | | |
|---|---|---|
| 8,354,129 B2 | 1/2013 | Quinlan et al. |
| 9,421,297 B2 | 8/2016 | Zhang et al. |
| 2002/0015762 A1 | 2/2002 | Quinlan |
| 2005/0107472 A1 | 5/2005 | Wischik et al. |
| 2005/0123603 A1 | 6/2005 | Dalland et al. |
| 2005/0176778 A1 | 8/2005 | Vermeer |
| 2006/0166948 A1 | 7/2006 | Vermeer |
| 2010/0048704 A1 | 2/2010 | Vermeer et al. |
| 2010/0130618 A1* | 5/2010 | Vaidya ............... A61K 31/122 514/681 |
| 2016/0250160 A1 | 9/2016 | Vermeer |
| 2018/0042962 A1 | 2/2018 | Majeti et al. |
| 2018/0271805 A1 | 9/2018 | Mezo |
| 2020/0289434 A1 | 9/2020 | Chlopicki et al. |
| 2022/0160651 A1 | 5/2022 | Chlopicki et al. |

FOREIGN PATENT DOCUMENTS

| | | |
|---|---|---|
| EP | 1728507 A1 | 12/2006 |
| WO | 2004019923 A1 | 3/2004 |
| WO | WO 2014/022373 A1 | 2/2014 |
| WO | 2019191773 A1 | 10/2019 |

OTHER PUBLICATIONS

International Search Report and Written Opinion issued in International Application No. PCT/US2019/025220 dated Sep. 4, 2019.
Sano et al. "Vitamin K2 (menatetrenone) induces iNOS in bovine vascular smooth muscle cells: no relationship between nitric oxide production and gamma-carboxylation." J Nutr Sci Vitaminol, (Tokyo), 1999, vol. 45(6), p. 711-723.
Ralf Westenfeld, MD et al., "Effect of Vitamin K2 Supplementation on Functional Vitamin K Deficiency in Hemodialysis Patients: A Randomized Trial", Am J Kidney Dis. 2012; 59(2), pp. 186-195.
Mabel Aoun et al., "High Dephosphorylated-Uncarboxylated MGP in Hemodialysis patients: risk factors and response to vitamin K2, A pre-post intervention clinical trial." BMC Nephrology, 2017, 18:191, pp. 1-10.
Mansour Anthony G et al: "Vitamin K2 supplementation and arterial stiffness among renal transplant recipients—a single-arm, single-center clinical trial", Journal of the American Society of Hypertension, Elsevier, Amsterdam, NL, vol. 11, No. 9, Jul. 13, 2017 (Jul. 13, 2017), pp. 589-597, XP085188006, ISSN: 1933-1711, DOI: 10.1016/J.JASH.2017.07.001.
McFarlin BK: "Oral Consumption of Vitamin K2 for 8 Weeks Associated With Increased Maximal Cardiac Output During Exercise", Abstract Altern Ther Health Med, Jul. 1, 2017 (Jul. 1, 2017), pp. 26-32, XP055697901, Retrieved from the Internet [retrieved on May 25, 2020].
Anna Bar et al: "Vitamin K2-MK-7 improves nitric oxide-dependent endothelial function in ApoE/LDLR-/- mice", Vascular Pharmacology, vol. 122-123, Nov. 1, 2019 (Nov. 1, 2019), NL, pp. 106581, XP055697798, ISSN: 1537-1891, DOI: 10.1016/j.vph.2019.106581.
Alfacalcidol, Compound Summary, PubChem, 2022, Retrieved from the Internet: <URL: https://pubchem.ncbi.nlm.nih.gov/compound/Alfacalcidol>, 35 pages.
Lind et al., "Reduction of blood pressure by treatment with alphacalcidol. A double-blind, placebo-controlled study in subjects with impaired glucose tolerance," Abstract, Acta Medica Scandinavica, 1988, vol. 223, No. 3, 1 page.
Shea et al., "Vitamin K and Vitamin D Status: Associations with Inflammatory Markers in the Framingham Offspring Study," American Journal of Epidemiology, Feb. 2008, vol. 167, No. 3, pp. 313-320.

(Continued)

Primary Examiner — Shobha Kantamneni
(74) Attorney, Agent, or Firm — ArentFox Schiff LLP

(57) ABSTRACT

A method for rapidly improving cardiovascular function, reducing arterial stiffness and reversing calcification of a blood vessel in a mammal comprising administering to the mammal an effective amount of vitamin K for a period of less than 6 months. Also a method for increasing endothelial nitric oxide production in mammals comprising administering to the mammal an effective amount of vitamin K for a period of less than 6 months. The vitamin K can be administered together with additional substances such as vitamin D.

8 Claims, 17 Drawing Sheets

(56) References Cited

OTHER PUBLICATIONS

Ushiroyama et al., "Effect of continuous combined therapy with vitamin K2 and vitamin D3 on bone mineral density and coagulofibrinolysis function in postmenopausal women," Maturitas, Mar. 2002, vol. 41, pp. 211-221.
Kleinbongard et al., "Plasma nitrite concentrations reflect the degree of endothelial dysfunction in humans," Free Radical Biology & Medicine, Jan. 2006, vol. 40, No. 2, pp. 295-302.

* cited by examiner

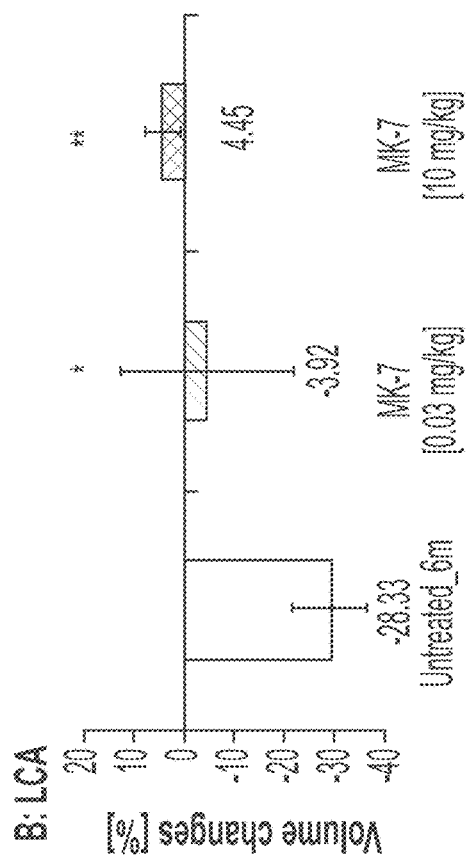
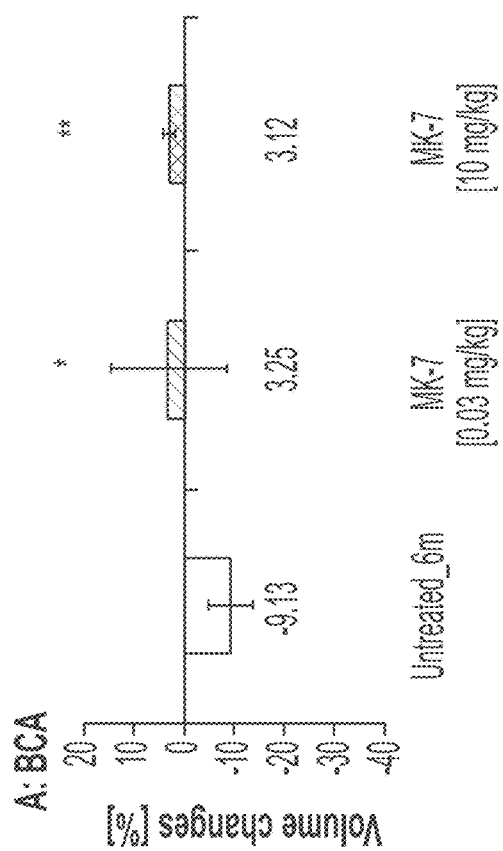
FIG. 2A
FIG. 2B

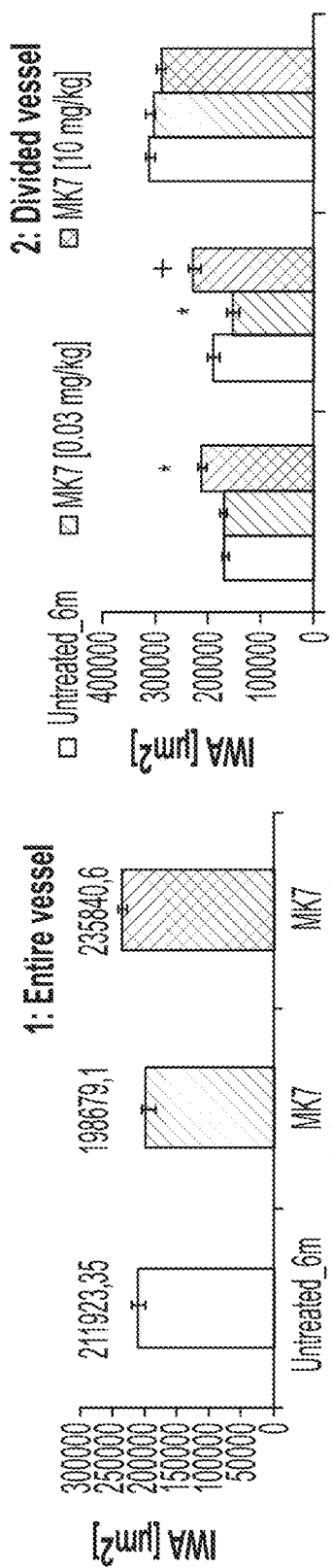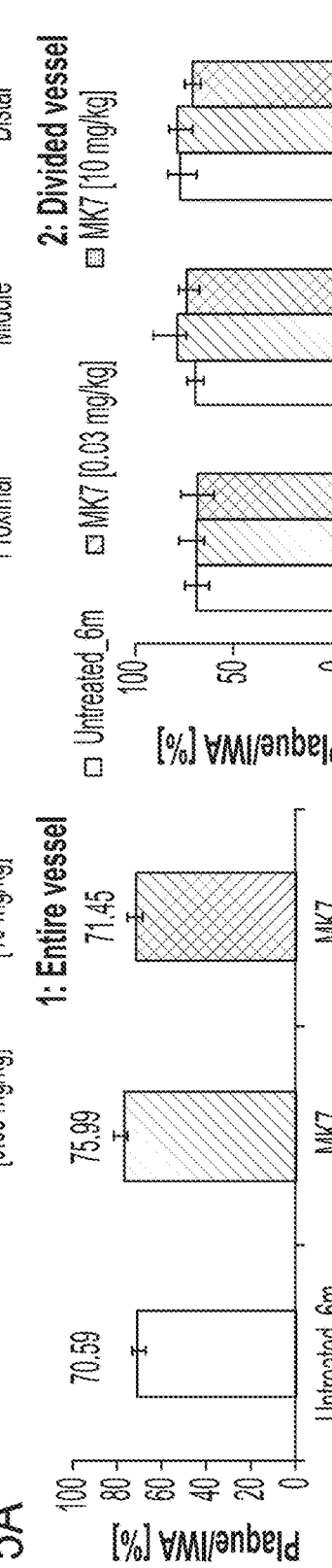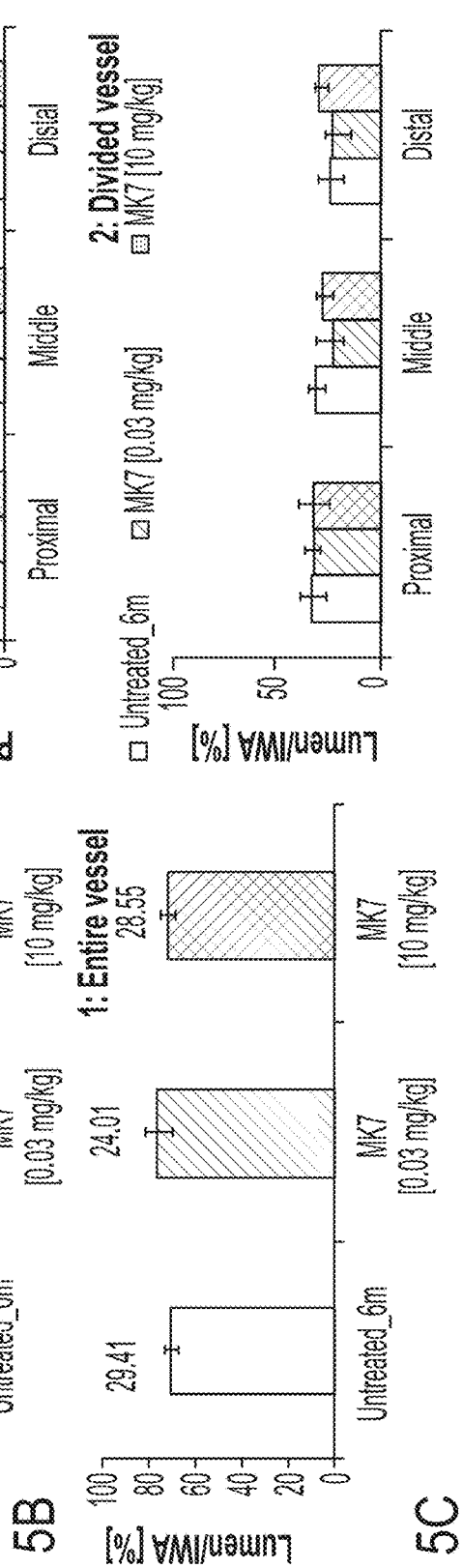
FIG. 5A
FIG. 5B
FIG. 5C

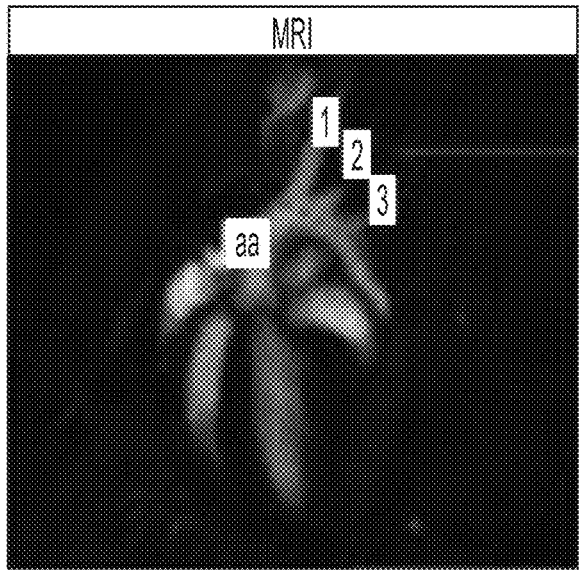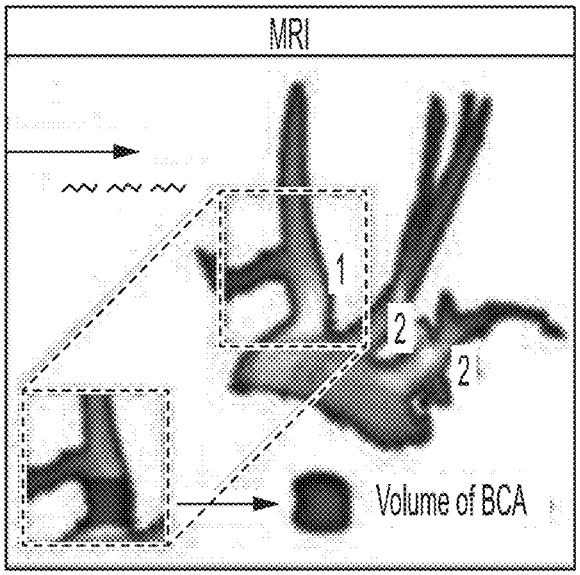
FIG. 6A            FIG. 6B
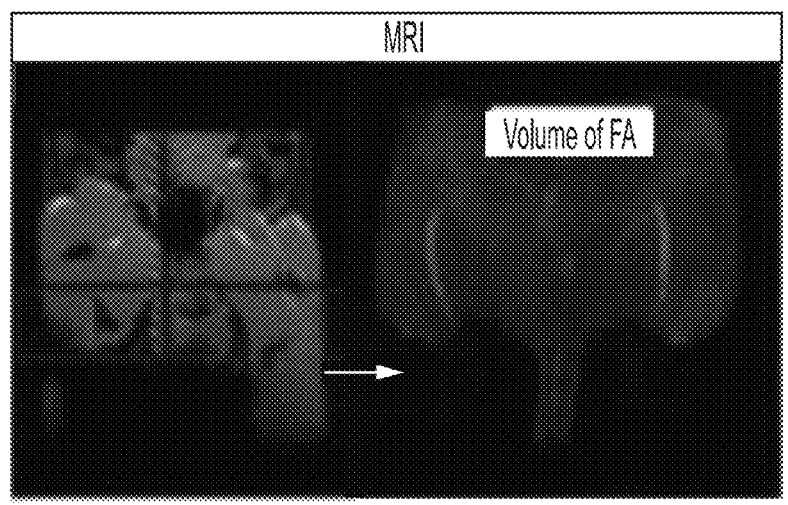
FIG. 6C            FIG. 6D

RAPIDLY IMPROVING VASCULAR CONDITIONS BY ADMINISTERING VITAMIN K

FIELD OF THE INVENTION

The present invention is directed to the administration of vitamin K to quickly improve vascular conditions, such as endothelial function, reduce arterial stiffness, and reverse calcification of blood vessels in mammals in less than six months, preferably less than 6 weeks. The present invention is also directed to the administration of vitamin K to increase endothelial nitric oxide production in mammals.

BACKGROUND OF THE INVENTION

The process of aging in mammals is associated with irreversible physiological changes to the circulatory system, leading to an increased risk of blood pressure disorders, Coronary Heart Disease (CHD) and stroke. For women, this risk rises dramatically after the onset of menopause. These conditions have a significant impact on quality of life for the middle-aged and elderly and account for a large proportion of deaths and chronic illnesses in modern societies.

Patients suffering from cardiovascular disorders are frequently prescribed anticoagulants, anti-hypertensives, cholesterol lowering medications, and other medications. These medications usually present harmful side-effects or health risks and moreover, the chronic effects of taking such medications regularly over the course of years or decades are not well understood. As life expectances increase, it would be desirable to find safe and reliable natural therapies to prevent, treat or even reverse the consequences of aging on the vasculature.

Changes in mechanical properties of the main arteries have major implications for the development of vascular disease. Blood vessels are made of three layers, the tunica intima, the tunica media and the tunica adventitia. Calcification can occur in or on any of these layers. Typically, calcification of the blood vessel makes the vessel wall rigid, fragile and subject to rupture. For purposes of the present invention, blood vessels include capillaries, veins, arteries, venules, and/or arterioles. Arteries, especially the larger elastic arteries such as the common carotid artery, become stiffer with age. Measures of large artery stiffening include compliance and distensibility. Compliance reflects the buffering capacity of the vascular vessel wall, and distensibility refers to the intrinsic vascular wall elasticity. In cross-sectional studies it has been shown that the distensibility and compliance of the elastic common carotid artery decrease linearly with age. The increase in arterial stiffness with increasing age is suggested to occur more rapidly in women aged between 45 and 60 years than in men of the same age group due to the lack of estrogen after menopause.

Reductions in compliance and distensibility result in an impairment of the arterial system to cushion pulsatile pressure. Arterial stiffening results in a higher pulse wave velocity and earlier wave reflections. This increases systolic and pulse pressure and consequently cardiac workload. To compensate, the arterial diameter increases with age. Over time, arterial stiffening can contribute to the development of, inter alia, left ventricular hypertrophy, congestive heart failure and coronary heart disease.

It has long been recognized that vitamin K is an essential component of the diet. It was first identified as an element needed to prevent hemorrhaging by activating blood-clotting factors. Natural K-vitamins are menadione-derivatives differing from each other in the polyisoprenoid side chain attached to the 3-position of the ring structure. Vitamin K can be provided in the diet by dark green, leafy vegetables (K1 or phylloquinone), and by fermented foods such as cheese and curd (K2 or menaquinone). K2 vitamins are also synthesized in the small intestine by resident symbiotic bacteria. Vitamin K is also needed for carboxylation of two bone matrix proteins necessary for normal bone metabolism.

Example 1 of U.S. application Ser. No. 15/151,970, published as US 2016/0250160 (herein incorporated by reference), discloses that, after 3 years, the co-administration of Vitamin K and Vitamin D was effective in slowing and maybe even reversing the process of stiffening of the arteries, while the administration of Vitamin D alone was not. See paragraph [0080]. The preferred treatment time for limiting an increase in arterial stiffness is a minimum of 6 months, more preferably at least 12 or 18 months, and ideally at least 36 months. See paragraph [0045]. The application also discloses that vitamin K can be used to reduce or reverse calcification of a blood vessel. See paragraph [0054]. The preferred treatment period for removal of calcification can be a minimum of 6-12 weeks, preferably at least 6-8 months and most preferably at least 12 months or longer. See paragraph [0060].

EP-A-0 679 394 and Jpn. J. Pharmacol. (1997) 75: 135-143 disclose that a high dietary intake of vitamin K and related molecules can reduce further arterial calcification, but not reverse it, from which it is concluded that arteriosclerosis can be treated using vitamin K. Arteriosclerosis is a disease of the arteries characterized by inflammation, macrophage invasion, foam cell formation, intima thickening, accretion of cholesterol and formation of the atherosclerotic plaque, which over time can become calcified. The onset of atherosclerosis is invariably in the large arteries such as for example, the aorta and coronary arteries. In more advanced stages one may see plaque rupture leading to sudden vascular occlusion, myocardial infarction and cerebrovascular accident (infarction of the brain).

A completely different process is that of vascular stiffening due to loss of elasticity of the arteries. Vascular stiffening is associated with ageing, diabetes mellitus and renal dysfunction; it is the result of degradation of the elastic lamellae in the tunica media resulting in loss of elasticity. The onset of vascular stiffening is generally seen in the smaller vessels but extends to the large arteries. This will lead to increased blood pressure, vascular widening, and in later stages to rupture of mainly the small arteries and capillaries.

Studies have shown that on a molecular level, age-related stiffening of the arteries can be distinguished from arteriosclerotic/atherosclerotic calcification. Whereas atherosclerosis is invariably associated with inflammation and starts with destruction of the endothelium at the luminal side of the tunica intima, age-related stiffening is a process, which originates in the tunica media, and is not associated with inflammation. It is believed that age-related stiffening occurs as a result of deposition of minerals around the elastic fibers of the tunica media, followed by degradation of the elastin structure. After deterioration of the elastin, the elastic properties of the artery depend on collagen, which is much less flexible.

The endothelium is involved in most if not all disease states, either as a primary determinant of pathophysiology or as a victim of collateral damage (Chlopicki S. *Perspectives in pharmacology of endothelium: From bench to bedside.* Pharmacol Reports 2015; 67:vi-ix; Frolow M, Drozdz A, Kowalewska A, Nizankowski R, Chlopicki S. Comprehensive assessment of vascular health in patients; towards endothelium-guided therapy. Pharmacol Rep 2015; 67:786-92). Endothelial dysfunction is associated with diseases/conditions including peripheral vascular disease, stroke, heart disease, diabetes, insulin resistance, chronic kidney failure, kidney transplants, tumor growth, metastasis, venous thrombosis, septic shock, hypertension, smoking, chronic exposure to air pollution, physical inactivity cardiovascular disease, coronary artery disease, chronic heart failure, hemodialysis, kidney transplants, hyperparathyroidism, hyperphosphatemia and severe viral infectious diseases. Endothelial dysfunction is characterized by improper regulation of vascular tone due to an imbalance of vasodilating and vasoconstricting substances associated with vascular endothelial cells (e.g. low production/availability of nitric oxide or increased availability of endothelium derived contracting factors). Endothelial dysfunction can precede the development of atherosclerosis.

The endothelium lines the interior surface of all blood vessels and lymphatic vessels. Vascular endothelial cells form a single layer interface between circulating blood and the vessel wall. The endothelium has a central role in the regulation of blood flow through continuous modulation of vascular tone. This is primarily accomplished by balanced release of endothelial relaxing and contractile factors. Healthy endothelial cells are essential for the maintenance of vascular homeostasis. The vascular endothelium has several functions including acting as a barrier to control the passage of materials and white blood cells, fluid filtration, vasoconstriction and vasodialation (controlling blood pressure), and control of thrombosis and thrombolysis. Vascular endothelial cells prevent thrombosis by means of different anticoagulant and antiplatelet mechanisms. These cells are involved in hemostatic pathways triggered upon vascular injury and limit clot formation to the areas where hemostasis is needed to restore vascular integrity. Thus, vascular endothelial cells play a regulatory role in the circulation as a physical barrier and as a source of regulatory substances. Endothelial cells can produce and release nitric oxide and prostacyclin which are associated with vascular relaxation and inhibit platelet activation. Under specific conditions, endothelial cells can also release endothelium-derived contracting factors (EDCFs), including endothelins, angiotensin II, thromboxane A2 cyclooxygenase-derived prostanoids and superoxide anions. Vascular endothelial cells are also a source of growth inhibitors and promoters and thus play a role in the regulation of vascular growth.

Clinical investigations regarding the improvement and/or complete reversal of endothelial dysfunction are constantly being undertaken. A pharmacological approach for improving/reversing endothelial dysfunction has been shown to be beneficial in clinical trials investigating the actions of different cardiovascular drugs (e.g. Rosuvastatin, Perindopril, Nebivolol, Carvedilol, Pioglitazone, Telmisartan, Gliclazide, Pitavastatin, Telmisartan, Atorvastatin, Lisinopril, Spironolactone, L-thyroxin, Infliximab, and Simvastatin). The finding of the effect of vitamin K on endothelial function indicates a novel therapeutic perspective for vitamin K as a vasoprotective agent in various diseases associated with endothelial dysfunction.

SUMMARY OF THE INVENTION

The present invention provides for the use of vitamin K in the preparation of a pharmaceutical or nutritional formulation for improving cardiovascular function, elasticity, pulse wave velocity or endothelial dysfunction, reducing arterial stiffness and/or for reversing calcification of a blood vessel in a mammal, wherein the improvement occurs in less than 6 months, preferably less than 6 weeks. The present invention also provides for the use of vitamin K in the preparation of a pharmaceutical or nutritional formulation for increasing endothelial nitric oxide production in a mammal.

Administration of vitamin K can lead to a rapid improvement in cardiovascular function, elasticity, pulse wave velocity or endothelial function, a rapid reduction in arterial stiffness and/or rapid removal of calcified precipitates from blood vessels that have already been affected by pre-existing calcification. Treatment with vitamin K can rapidly reverse existing artery disease and reduce the risk of an incident requiring intense medical treatment. Though vitamin K was previously administered for improving arterial compliance and distensibility, it was believed that, in order for such improvement to occur, the vitamin K had to be administered for a minimum of 6 months, more preferably at least 12 or 18 months, and ideally at least 36 months. See US 2016/0250160.

In one aspect, the invention provides a method for improving cardiovascular function, elasticity, pulse wave velocity or endothelial dysfunction, reducing arterial stiffness and/or for reversing calcification of a blood vessel in a mammal by administering vitamin K or a derivative thereof, optionally together with vitamin D or a derivative thereof, in a medicament or nutritional formulation for a period of less than 6 months, less than 5 months, less than 4 months, less than 3 months, less than 2 months, less than 6 weeks, less than 4 weeks, or less than 2 weeks. Preferably, improvement occurs in less than 6 months, less than 5 months, less than 4 months, less than 3 months, less than 2 months, less than 6 weeks, less than 4 weeks, or less than 2 weeks. In some embodiments, the vitamin K is administered for 2-16 weeks, preferably 2-12 weeks, 2-8 weeks, 2-less than 6 weeks, or 2-4 weeks.

In another aspect, the invention provides a method for treating age related stiffening of arteries, an age-related decrease in compliance and/or distensibility of arteries and/or an age-related increase in pulse pressure, comprising administering vitamin K or a derivative thereof, optionally together with vitamin D or a derivative thereof, in a medicament or nutritional formulation for a period of less than 6 months, less than 5 months, less than 4 months, less than 3 months, less than 2 months, less than 6 weeks, less than 4 weeks, or less than 2 weeks. Preferably, improvement occurs in less than 6 months, less than 5 months, less than 4 months, less than 3 months, less than 2 months, less than 6 weeks, less than 4 weeks, or less than 2 weeks. In some embodiments, the vitamin K is administered for 2-16 weeks, preferably 2-12 weeks, 2-8 weeks, 2-less than 6 weeks, or 2-4 weeks.

In another aspect, the invention provides a method for reversing pre-existing calcification of blood vessels, comprising administering vitamin K or a derivative thereof, optionally together with vitamin D or a derivative thereof, in a medicament or nutritional formulation for a period of less than 6 months, less than 5 months, less than 4 months, less than 3 months, less than 2 months, less than 6 weeks, less than 4 weeks, or less than 2 weeks. Preferably, improvement occurs in less than 6 months, less than 5 months, less than 4 months, less than 3 months, less than 2 months, less than 6 weeks, less than 4 weeks, or less than 2 weeks. In some embodiments, the vitamin K is administered for 2-20 weeks or 2-16 weeks, preferably 2-12 weeks, 2-8 weeks, 2-less than 6 weeks, or 2-4 weeks. Calcification of a blood vessel can be associated with diseases/conditions such as arteriosclerosis including Monckeberg's sclerosis, osteoarthritis, inflammation-induced calcification, including Bechterev's disease, tumor-induced calcification, kidney (renal) transplants, hyperparathyroidism, hyperphosphatemia, skin calcification, including pseudo-xanthoma elasticum (PXE), chronic kidney disease (CKD), including Stage 1 CKD, Stage 2 CKD, Stage 3 CKD, Stage 4 CKD, and Stage 5 CKD, and calcifylaxis in end stage renal disease.

In another aspect, the invention provides a method for treating a disease/condition selected from arteriosclerosis such as Monckeberg's sclerosis, osteoarthritis, inflammation-induced calcification such as Bechterev's disease, tumor-induced calcification, kidney (renal) transplants, hyperparathyroidism, hyperphosphatemia, skin calcification such as pseudo-xanthoma elasticum (PXE), chronic kidney disease (CKD) such as Stage 1 CKD, Stage 2 CKD, Stage 3 CKD, Stage 4 CKD, and Stage 5 CKD, and calcifylaxis in end stage renal disease, comprising administering vitamin K or a derivative thereof, optionally together with vitamin D or a derivative thereof, in a medicament or nutritional formulation for a period of less than 6 months, less than 5 months, less than 4 months, less than 3 months, less than 2 months, less than 6 weeks, less than 4 weeks, or less than 2 weeks. Preferably, improvement occurs in less than 6 months, less than 5 months, less than 4 months, less than 3 months, less than 2 months, less than 6 weeks, less than 4 weeks, or less than 2 weeks. In some embodiments, the vitamin K is administered for 2-16 weeks, preferably 2-12 weeks, 2-8 weeks, 2-less than 6 weeks, or 2-4 weeks.

In another aspect, the invention provides a method for increasing endothelial nitric oxide production in a subject, the method comprising administering vitamin K or a derivative thereof in a medicament or nutritional formulation to the subject. According to some aspects, the subject may either present with atherosclerotic plaques or may present without atherosclerotic plaques. According to some aspects, the subject may suffer from hypercholesterolemia. Treatment may be for a period of less than 6 months, less than 5 months, less than 4 months, less than 3 months, less than 2 months, less than 6 weeks, less than 4 weeks, or less than 2 weeks. Preferably, improvement in endothelial nitric oxide production occurs in less than 6 months, less than 5 months, less than 4 months, less than 3 months, less than 2 months, less than 6 weeks, less than 4 weeks, or less than 2 weeks. In some embodiments, the vitamin K is administered for 2-16 weeks, preferably 2-12 weeks, 2-8 weeks, 2-less than 6 weeks, or 2-4 weeks.

In a further aspect, the medicament or nutritional formulation can contain one or more additional components selected from: polyphenols, vitamin C, vitamin D, vitamin E (tocopherols and/or tocotrienols), L-Arginine, phytosterols, antihypertensive peptides, soluble fibers (e.g. guar, pectin), omega-3, omega-6 and/or omega-9 fatty acids, carnitine, taurine, coenzyme Q10, creatine, folic acid, folates, magnesium, potassium, vitamin B6, and vitamin B12. The medicament or nutritional formulation can be administered simultaneously, separately or sequentially with a medicament selected from the group consisting of anticoagulants, antithrombotics, fibrinolytics, anthypertensives, diuretics, anticanginals, hypolipidaemic agents, beta-blockers, ACE inhibitors, cardiac glycosides, phosphodiaeterase inhibitors, antiarrhythmics and calcium antagonists.

In another aspect of the invention, a composition is provided for improving cardiovascular function, elasticity, pulse wave velocity or endothelial dysfunction, reducing arterial stiffness and/or for reversing calcification of a blood vessel in a mammal. The composition preferably contains 10 µg to 2000 mg of vitamin K, more preferably 100 µg to 50 mg, 200 µg to 20 mg, or 400 µg to 10 mg.

Additional features and advantages of various embodiments will be set forth in part in the description that follows and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

FIG. 2(A)-2(B) show the effects of treatment with low and high doses of vitamin MK-7 on endothelial function in vivo in ApoE/LDLR-/- mice. Changes in end-diastolic volume of a brachiocephalic artery (A: BCA) and left common carotid artery (B: LCA) 25 min after Ach administration in non-treated ApoE/LDLR-/- mice (white columns) and in ApoE/LDLR-/- mice treated with vitamin MK-7 given at the low (0.03 mg/kg b.w./day, black columns) or the high dose (10 mg/kg b.w./day, columns with diagonal lines) for two months (Untreated_6 m: n=10, MK-7 [0.03 mg/kg]: n=8, MK-7 [10 mg/kg]: n=6). Statistics: one-way ANOVA (HSD Tukey's test); $*p<0.05$, $**p<0.01$ vs. Untreated_6 m mice.

Figure 1A:
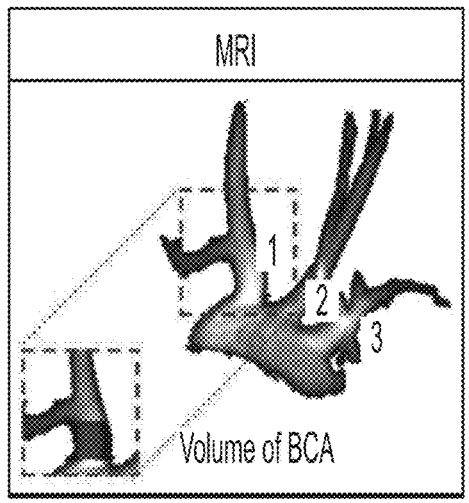
FIG. 1(A)-1(C) show the endothelium dependent response in vivo as assessed using MRI. (A); analysis of plaque size and composition by quantitative histologic evaluation (B); analysis of media thickness and vascular wall structure (C). A: 3D image of an aortic arch, with the following vessels: (1) brachiocephalic artery (BCA), (2) left common carotid artery (LCA) and (3) subclavian artery (LSA), acquired with the cine IntraGate® FLASH 3D sequence. Endothelial function assessment was expressed as changes in the vessel's volume. B: Representative images of the BCA cross-sections stained with OMSB, showing atherosclerotic plaque (P) with lipid core (Lc) and collagen (C), artery lumen (L) and wall (W). Internal wall area (IWA) was determined as sum of plaque area and lumen area, while VWA is a media layer marked in red (W). C: Remodelling of vascular wall with increased media thickness associated with atherosclerosis development. Subsequent slices in the middle part of the BCA, showing vascular wall remodelling with visible increased thickness of smooth muscle vascular layers between elastic laminas—the histopathological basis of changes in VWA

FIG. 5(A)-5(E) show the effects of treatment with low and high doses of vitamin MK-7 treatment on plaque size and composition in ApoE/LDLR-/- mice. Changes in internal wall area (A: IWA), plaque area (B: expressed as percent of internal wall area:plaque/IWA), lumen area (C: expressed as percent of internal wall area: lumen/IWA), as well as areas of collagen and lipids in plaque (D: Collagen/plaque and E: Lipid/plaque, respectively) in non-treated ApoE/LDLR-/- mice (white columns) and in ApoE/LDLR-/- mice treated with vitamin MK-7 given at low (0.03 mg/kg b.w./day, black columns) or high dose (10 mg/kg b.w./day, columns with diagonal lines) for two months (Untreated_6 m: n=6, MK-7 [0.03 mg/kg]: n=7, MK-7 [10 mg/kg]: n=6). The assessment was performed for the entire vessel (A) and for a divided vessel (B) in proximal, middle and distal parts. Statistics: Statistics: Kruskal Wallis test; *p<0.05, p<0.01, *p<0.001 vs. Untreated_6 m mice.

FIG. 6(A)-6(D) show the methodology of MRI-based assessment of endothelium-dependent response in vivo. (A) Coronal view of heart. Image showing position of the imaging layer (red cuboid) used for 3D MRI imaging of the aortic arch (aa). Additionally, following vessels are visible: (1) brachiocephalic artery (BCA), (2) left common carotid artery (LCA) and (3) subclavian artery (LSA). (B) 3D image of aa acquired with the cine IntraGate® FLASH 3D sequence. (C) Sagittal view of the cross-section of mice with abdominal aorta (AA). (D) Coronal view of the cross-section of mice with femoral artery (FA). Endothelial function assessment, expressed as changes in the vessels volume, was performed in BCA, LCA, AA and FA.

FIG. 7(A)-7(E) show the effects of treatment with vitamin K2 (MK-7) for a period of two to eight weeks, given at a dose of 0.05, 0.5, and 5 mg/kg b.w./day on endothelium-dependent vasodilatation in vivo and on nitric oxide production in aorta ex vivo in young ApoE/LDLR-/- mice. Changes in FMD response in the femoral artery (A,C) FMD-FA and Ach-response in abdominal aorta (B,D) ACH-AA measured in vivo by MRI and NO production (E) NO-AA in ex vivo aorta measured by EPR are shown. 11-week-old ApoE/LDLR-/- mice were treated with vitamin K2-MK-7 given at dose of 0.05 mg/kg b.w./day (n=8, black columns), 0.5 mg/kg b.w./day (n=5-8, columns in chessboard pattern) or 5 mg/kg b.w./day (n=6-8, columns with horizontal lines) for two (measurements at 13 weeks of age) and four weeks (measurements at 15 weeks of age) (A,B). 8-week-old ApoE/LDLR-/- mice were treated with vitamin K2 (MK-7) given at dose of 0.05 mg/kg b.w./day (n=6, black columns), for two weeks (measurements at 10 weeks of age) and eight weeks (measurements at 16 weeks of age) (C,D,E). Results were compared to untreated age-matched ApoE/LDLR-/- mice (n=7-8, white columns). Statistics: A,B,C,D: two-way ANOVA (post hoc: Tukey's test); E: Mann-Whitney U test, *p<0.05, p<0.01, *p<0.001.

FIG. 8(A)-8(E) show the dose-dependent effects of treatment with vitamin K2 (MK-7) on plasma concentration of vitamin K2 (MK-7) and K2 (MK-4) in young ApoE/LDLR-/- mice. Plasma concentration of vitamin K2 (MK-7) (A), K2 (MK-4) (B), K1 (C), K1 2,3-epoxide (D) and MK4 2,3-epoxide (E) are shown. 11-week-old ApoE/LDLR-/- mice were treated four weeks with K2 (MK-7) given at three doses (0.05 mg/kg b.w./day, n=8, black columns; 0.5 mg/kg b.w./day: n=6, chessboard pattern columns; 5 mg/kg b.w./day: n=8; columns with horizontal lines) and compared to untreated age-matched ApoE/LDLR-/- mice (n=8, white columns). <LOD—<limit of detection, n—number of samples for which concentration of vitamin K2 (MK-7) was above LOD. Statistics: Kruskal Wallis test; *p<0.05, p<0.01, *p<0.001.

Figure 9:
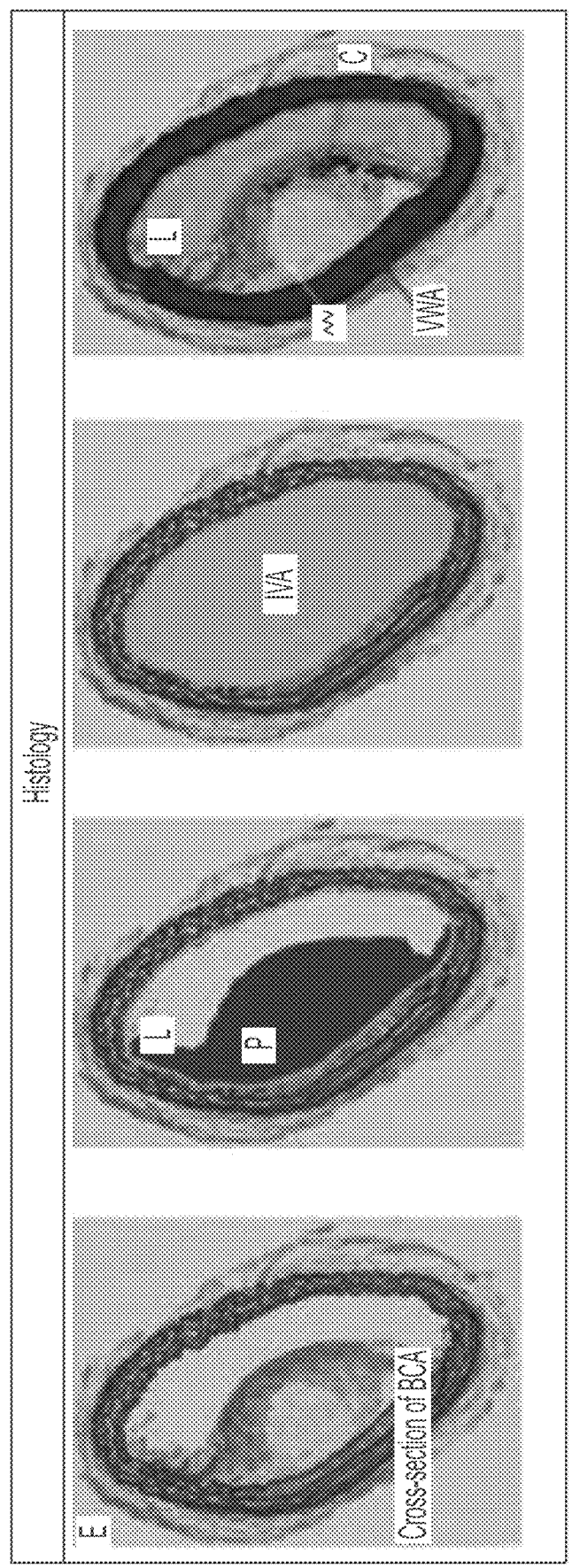
Figure 10A:
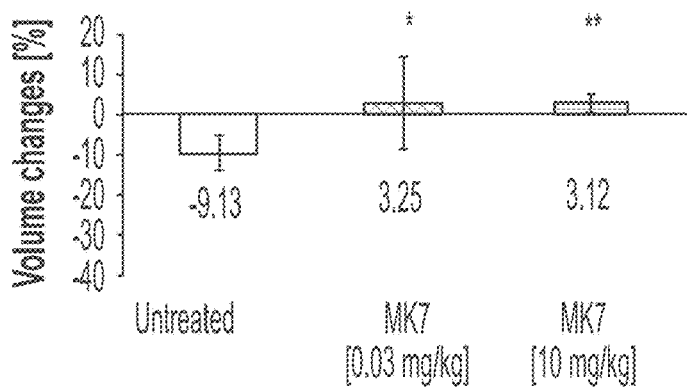
Figure 10B:
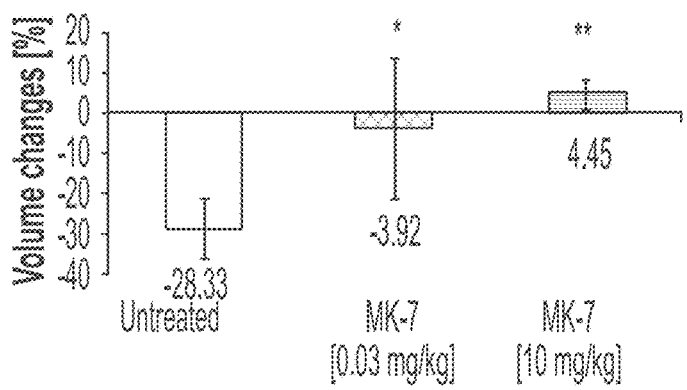
Figure 10C:
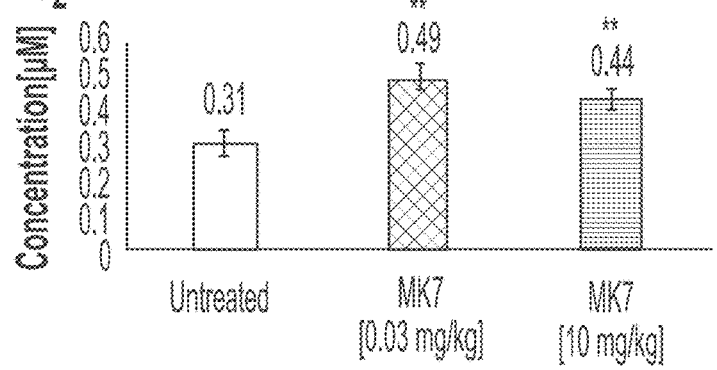
Figure 10D:
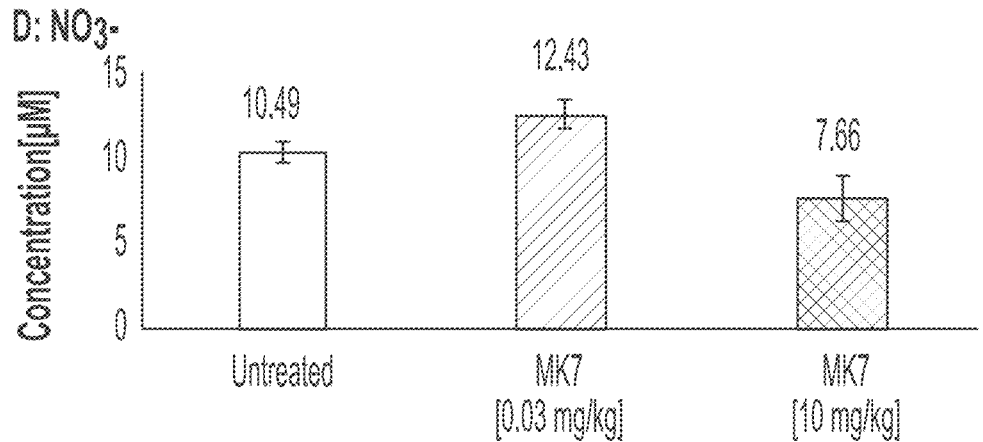
Figure 10E:
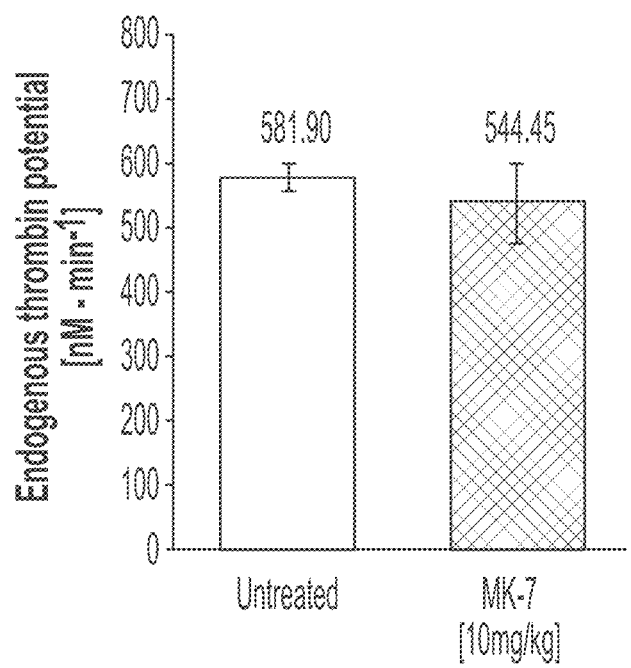
Figure 10F:
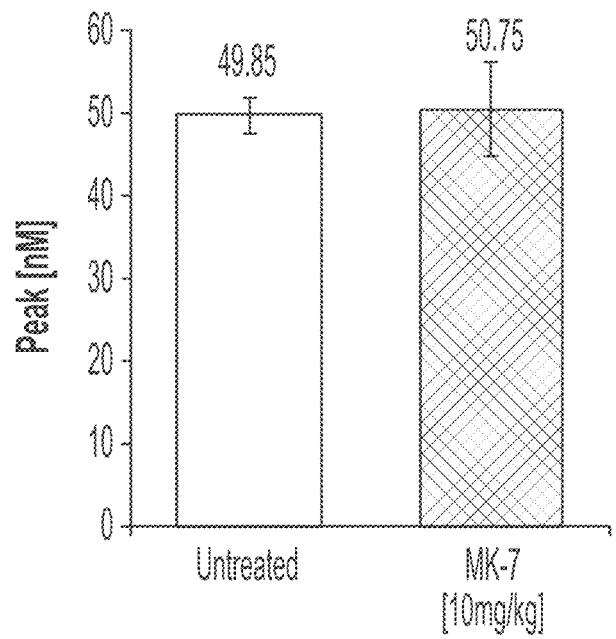
Figure 10G:
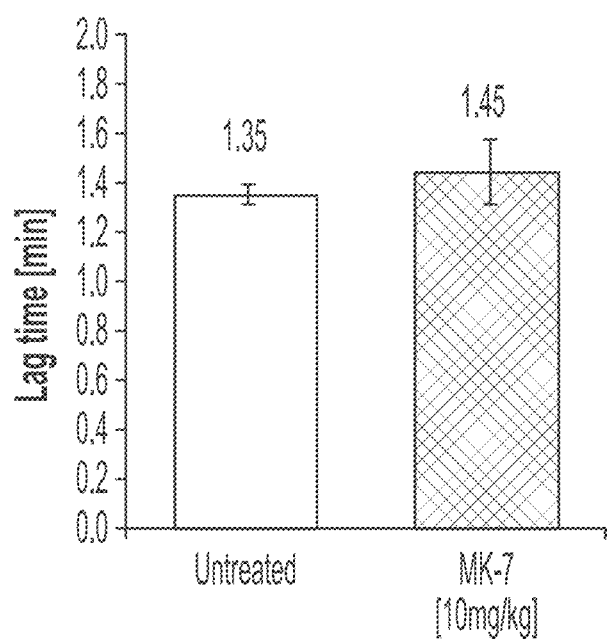

FIG. 9 shows the assessment of plaque size and composition using histologic evaluation, specifically representative images of the BCA cross-sections stained with Unna's orcein combined with Martius, Scarlet and Blue trichrom (OMSB). The areas of particular components of atherosclerotic plaque (P) including: Lipid core (Lc), collagen (C), as well as artery lumen (L) and vessel wall area (VWA) were determined after Columbus-based software processing. Internal vessel area (IVA) was determined as sum of plaque area and lumen area.

FIG. 10(A)-10(G) show the effects of treatment with low and high dose of vitamin K2 (MK-7) on endothelial function in vivo (A-B), nitrite ($NO_2^-$) and nitrate ($NO_3^-$) concentration in plasma (C-D) and coagulation measured by thrombin generation in plasma (E-G) in older ApoE/LDLR-/- mice. Changes in Ach-induced response in brachiocephalic artery (A) ACH-BCA and left common carotid artery (B) ACH-LCA are shown as well as changes in $NO_2^-$ (C) and $NO_3$ (D) concentration in plasma and thrombin activity shown as endogenous thrombin potential (E), peak thrombin concentration (F: Peak) and lag time (G). 24-week-old ApoE/LDLR-/- mice were treated for eight weeks with vitamin K2 (MK-7) in low dose (0.03 mg/kg b.w./day: n=8-9, black columns) or high dose (10 mg/kg b.w./day: n=6, gray columns) as compared to untreated age-matched ApoE/LDLR-/- mice (n=6-10, white columns). Statistics: A-D: one-way ANOVA; E-G: Mann-Whitney U test, *p<0.05, **p<0.01 vs. Untreated mice.

Figure 11:
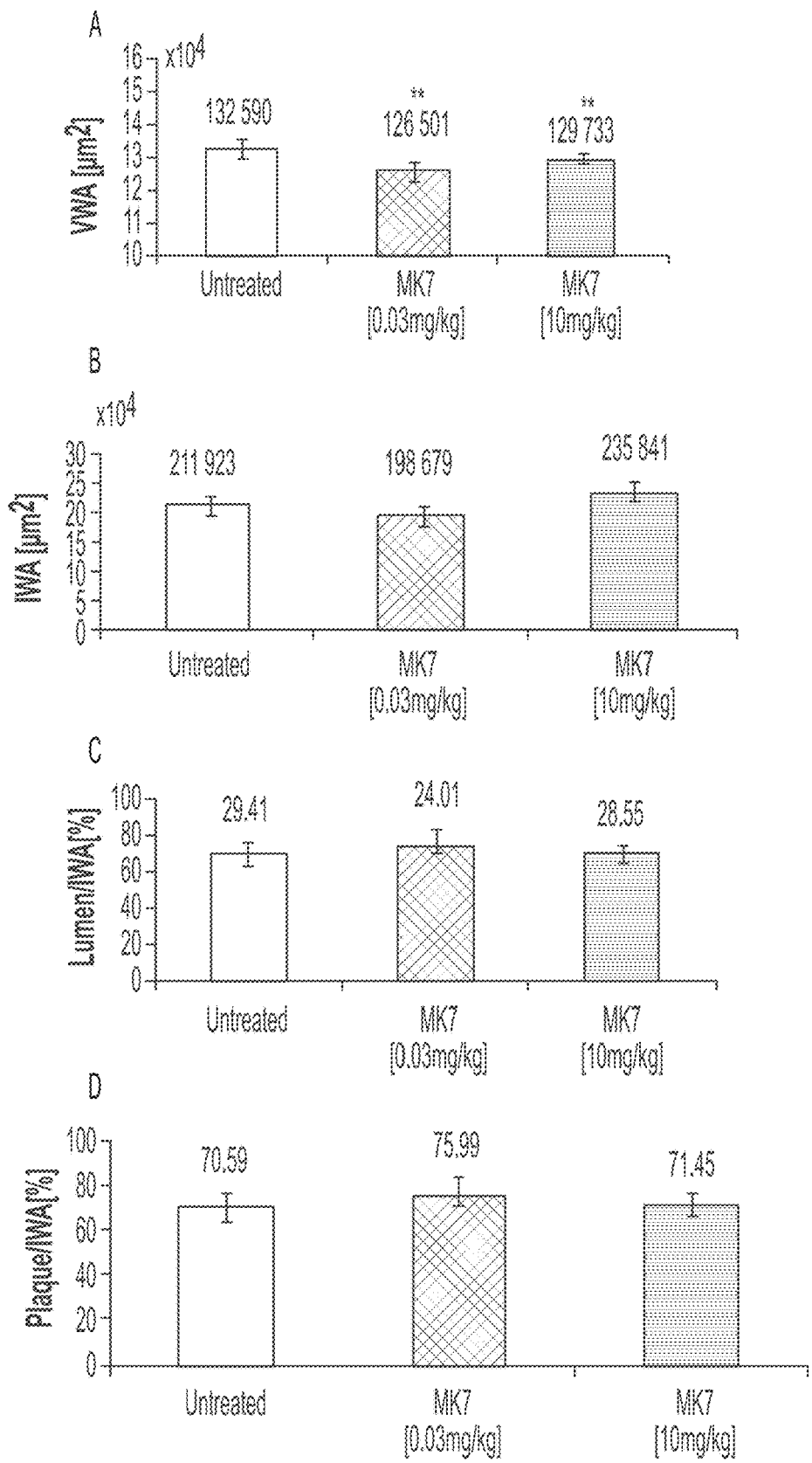

FIG. 11 shows the effects of treatment with low and high dose of vitamin K2 (MK-7) on vascular wall area (A) and plaque size (B-D) in older ApoE/LDLR-/- mice. Vessel wall area (A) VWA of BCA, changes in internal wall area (B) IWA, lumen area (C) expressed as percent of internal wall area: lumen/IWA and plaque area (D) expressed as percent of internal wall area: plaque/IWA, are shown. 24-week-old ApoE/LDLR-/- mice were treated for eight weeks with vitamin K2 (MK-7) in low dose (0.03 mg/kg b.w./day: n=7, black columns) or high dose (10 mg/kg b.w./day: n=6) as compared to untreated age-matched ApoE/LDLR-/- mice (n=6, white columns). Statistics: Kruskal Wallis test; *p<0.05, p<0.01, *p<0.001 vs. Untreated mice.

Figure 12:
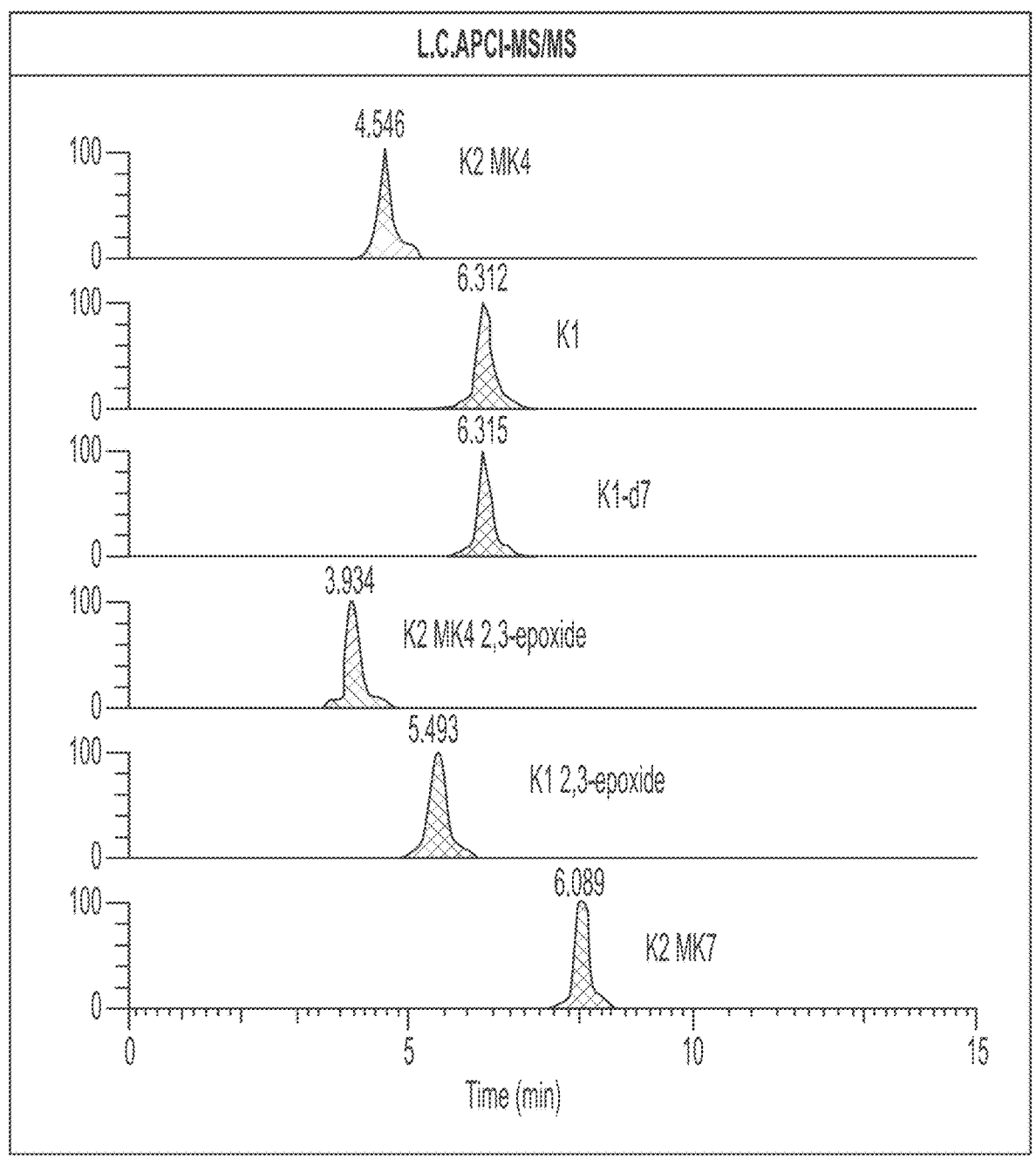

FIG. 12 shows LC-APCI-MS/MS-based assessment of plasma concentration of vitamin K, specifically LC-APCI-MS/MS chromatograms of the various vitamin K homologues.

DETAILED DESCRIPTION OF THE INVENTION

Vitamin K and derivatives refers to one or more compounds of Formula 1 and their pharmaceutically or nutritionally acceptable salts:

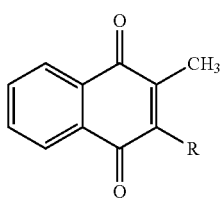

Formula 1 wherein R may be any covalently linked organic group including polyisoprenoid residues, esters, ethers, and thiol adducts, preferably R is a compound of Formula 2,

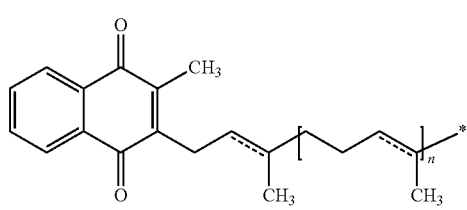

FIG. 2 wherein n is an integer from 1 to 12 and the broken lines indicate the optional presence of a double bond.

Vitamin K and derivatives thereof, as used herein, refers particularly to phylloquinome (Vitamin K1), dihydrophylloquinne, menaquinone (Vitamin K2) including the short chain menaquinones (particularly MK-4) and the long chain menaquinones (particularly MK-7). Sources of vitamin K which can be used according to the present invention include the following: phylloquinone, from natural sources such as vegetable extracts, fats and oils, synthetic phylloqinone, synthetic vitamin K3 (menadione) and different forms of vitamin K2: synthetic MK-4, MK-5, MK-6, MK-7, MK-8, MK-9, MK-10, MK-11, MK12 and MK-13, natto (food prepared from fermented soy-bean, rich in MK-7) and other fermented foods and or dairy products.

Vitamin K enriched foods can be manufactured to provide the daily requirements of vitamin K. For example, vitamin K can be added to food products such as meal replacers, ice cream, chocolates, chewing gums, margarines, sauces, dressings, spreads, bars, sweets, snacks, cereals, beverages such as juices, dairy drinks, powdered drinks, sports drink and energy drinks, by methods as described in EP 1 153 548 and U.S. Pat. No. 8,354,129, the entire disclosure of which is incorporated by reference herein. Alternatively, vitamin K can be included in food supplements such as multivitamins, tablets, capsules, elixirs, chews, gummies and other supplement forms. One preferred nutritional formulation comprises 50 µg-1.5 mg vitamin K; 5-10 µg vitamin D; 450-550 mg calcium; 7-12 mg zinc; and 100-200 mg magnesium.

The dose of vitamin K useful in carrying out the method is not restricted but varies depending on for example, the age of subject and the degree of cardiovascular dysfunction, endothelial dysfunction, the degree of arterial stiffening, the degree of calcification of the blood vessel and the degree of reverse calcification desired. Currently the recommended daily dose of vitamin K is 120 µg for men and 90 µg for women. The benefits of improved cardiovascular function, elasticity, endothelial function, reduced arterial stiffness, increased endothelial nitric oxide production, and/or reduced calcification can be derived at doses higher than the recommended values, particularly in groups where vitamin K deficiencies are common, such as post-menopausal women, or may be derived at doses lower than the recommended values. For example, suitable doses may be in the range of 10 µg to 2000 mg of vitamin K, more preferably 100 µg to 50 mg, 200 µg to 20 mg, or 400 µg to 10 mg. In some embodiments, suitable doses may be 150 to 5000 µg/day, 150-500 µg/day, 10 to 2000 µg/day, optionally 50-1000 µg/day, optionally 150-500 µg/day, and optionally 180-360 µg/day; 70 to 14,000 µg/week or 350 to 7000 µg/week. In terms of body weight, daily dosage may vary from 0.03 to 10 mg/kg body weight/day or 0.5 to 300 µg/kg body weight/day, preferably 1 to 100 µg/kg and most preferably 2 to 40 µg/kg/day.

As used herein, the term "effective amount" or "therapeutically effective amount" are interchangeable and refer to an amount that results in an improvement, reversal or remediation of the symptoms of the disease or condition.

The vitamin K can be administered for a period of less than 6 months, less than 5 months, less than 4 months, less than 3 months, less than 2 months, less than 6 weeks, less than 4 weeks, or less than 2 weeks. Preferably, improvement occurs in less than 6 months, less than 5 months, less than 4 months, less than 3 months, less than 2 months, less than 6 weeks, less than 4 weeks, or less than 2 weeks. In some embodiments, the vitamin K is administered for 2-20 weeks or 2-16 weeks, preferably 2-12 weeks, 2-8 weeks, 2-less than 6 weeks, or 2-4 weeks. If desired, the dosage can be started at an initial dosage until improvement occurs and/or is observed, then lowered to a maintenance dose after sufficient improvement has occurred.

Vitamin D can be included together with the vitamin K in the composition and may play a role in supporting the function of vitamin K. Any form of natural or synthetic vitamin D may be employed, including vitamin D1, vitamin D2 (calciferol), vitamin D3 (cholecalciferol) and vitamin D analogues (e.g. alfacalcidol, dihydrotachysterol, calcitriol). Natural sources of vitamin D include saltwater fish, organ meats, fish-liver oils and egg yolk. Suitable dosages of vitamin D are 2 to 50 µg/day, preferably 5 to 20 µg/day, and most preferably about 7 to 10 µg/day.

The medicament or nutritional formulation can contain one or more additional components. Such additional components are preferably selected from: polyphenols, vitamin C, vitamin E (tocopherols and/or tocotrienols), L-Arginine, phytosterols, antihypertensive peptides, soluble fibers (e.g. guar, pectin), omega-3, omega-6 and/or omega-9 fatty acids, carnitine, taurine, coenzyme Q10, creatine, folic acid, folates, magnesium, potassium, vitamin B6, and vitamin B12. The medicament or nutritional formulation can also be administered simultaneously, separately or sequentially with a medicament selected from the group consisting of anticoagulants, antithrombotics, fibrinolytics, anthypertensives, diuretics, anticanginals, hypolipidaemic agents, beta-blockers, ACE inhibitors, cardiac glycosides, phosphodiaeterase inhibitors, antiarrhythmics and calcium antagonists.

The preferred route of administration of vitamin K is enterally, especially orally, but parenteral or topical routes can also be used. "Oral administration" as used herein includes oral, buccal, enteral or intragastric administration. The term "parenteral administration" as used herein includes any form of administration in which the vitamin K is absorbed into the blood stream without involving absorption via the intestines. Exemplary parenteral administrations that are used in the present invention include, but are not limited to intramuscular, intravenous, intraperitoneal, intraocular, subcutaneous or intraarticular administration. If topical administration is desired, physical or chemical drug delivery systems can be used to enhance skin penetration.

Vitamin K is conventionally provided in the form of tablets or capsules, i.e. in a pharmaceutical or dietary supplement format. For pharmaceutical preparations or dietary supplements the vitamin K may be compounded with pharmaceutically acceptable carriers, excipients or diluents in the forms of pills, tablets (coated or uncoated), hard or soft capsules, dragees, lozenges, oral solutions, suspensions and dispersions, syrups or sterile parenteral preparations. Suitable excipients include inert diluents such as calcium carbonate, sodium carbonate, lactose, calcium phosphate, sodium phosphate; granulating and disintegrating agents such as cornstarch or alginic acid; binding agents such as starch gelatin or acacia; effervescents; and lubricating agents such as magnesium stearate, stearic acid or talc.

It is also possible to deliver or administer Vitamin K (optionally together with vitamin D) in a fortified food or beverage product. Preferred nutritional product formats include: juice drinks, dairy drinks, powdered drinks, sports drinks, mineral water, soy beverages, hot chocolate, malt drinks, biscuits, bread, crackers, confectioneries, chocolate, chewing-gum, margarines, spreads, yogurts, breakfast cereals, snack bars, meal replacements, protein powders, desserts, and medical nutrition tube feeds and nutritional supplements.

Conventional additives may be included in the compositions of the invention, including any of those selected from preservatives, chelating agents, effervescing agents, natural or artificial sweeteners, flavoring agents, coloring agents, taste masking agents, acidulants, emulsifiers, thickening agents, suspending agents, dispersing or wetting agents, antioxidants, and the like.

The vitamin K can be provided in the form of a kit containing an initial treatment dosage and a maintenance dosage. The initial treatment dosage is a dosage effective to induce improvement in cardiovascular function, elasticity, pulse wave velocity or endothelial function, reduction in arterial stiffness and/or the removal of pre-existing calcium deposits within the blood vessel wall in less than 6 months, less than 5 months, less than 4 months, less than 3 months, less than 2 months, less than 6 weeks, less than 4 weeks, or less than 2 weeks. In some embodiments, the vitamin K initial treatment dosage is administered for 2-20 weeks or 2-16 weeks, preferably 2-12 weeks, 2-8 weeks, 2-less than 6 weeks, or 2-4 weeks. The maintenance dosage is intended for long term administration after the initial treatment period is finished. Preferably, the dosages are in a form for oral administration, preferably in the form of tablets or capsules. Preferably, the maintenance dosage is provided in an amount sufficient for 1 week-36 months.

In various embodiments, the vitamin K is administered to a mammal including humans, as well as pet animals such as dogs and cats, laboratory animals, such as rats and mice, and farm animals, such as sheep, horses and cows. Patients who would benefit from improving endothelial function, reducing arterial stiffness and reversing calcification of blood vessels, include but are not limited anyone at risk from cardiovascular disorders or already suffering from conditions such as angina pectoris, hypertension, a history of stroke, and other cerebrovascular disorders. Particular target population groups are: postmenopausal women, diabetics, obese individuals, smokers, alcoholics, sedentary and inactive people, the elderly, hemodialysis patients, men over 40 years of age, people suffering from chronic stress, and those consuming an unhealthy diet prone to causing endothelial dysfunction, arterial stiffness and calcification of blood vessels. Patients who would benefit from improving endothelial function include those suffering from hypercholesterolemia, including patients suffering from familial hypercholesterolemia. As used herein, "hypercholesterolemia" refers to the condition characterized by high levels of cholesterol in the blood either in the absence or in the presence of atherosclerotic plaques.

In various embodiments of the present invention, by quickly improving cardiovascular function, elasticity, endothelial function or pulse wave velocity, reducing arterial stiffening and/or reversing calcification, vitamin K can be used to treat hypertension, left ventricular hypertrophy, congestive heart failure, myocardial infarction, stroke and coronary heart disease. "Elevated blood pressure" or "hypertension" as used herein refers to a blood pressure persistently exceeding 140/90 mmHg (systolic/diastolic). Diseases/conditions associated with pathological calcification, include but are not limited to, calcification of cartilage (osteoarthritis), inflammation-induced calcification (e.g. in Bechterev's disease), tumor-induced calcification (often seen in breast cancer), hyperparathyroidism, hyperphosphatemia, skin calcification such as in pseudoxanthoma elasticum (PXE), and calcifylaxis in end-stage renal disease.

Non-drug/nutritional treatment modalities for arteriosclerosis involve catheter-based procedures, such as angioplasty, that use a catheter inserted into an artery to press the plaque against the walls of the arteries to increase space for blood to flow. Stenting, usually done after angioplasty, uses a wire mesh tube placed in the damaged artery to support the arterial walls and is used to keep the vessel open. Atherectomy can be performed where instruments inserted via a catheter are used to cut away and remove plaque so that blood can flow more easily. Administering vitamin K according to the present invention can reduce or avoid the need for catheter-based or surgical treatment of atherosclerosis without delaying catheter-based or surgical treatment for extended periods of time, when necessary.

Endothelial dysfunction is a pathological condition associated with impaired vasodilation (imbalance between relaxing and contracting factors) as well as changes in the proinflammatory state and prothrombic properties. Endothelial function can be measured by any suitable means, including but not limited to intracoronary infusion of an endothelium dependent vasodialator (e.g. acetylcholine) and quantitative coronary angiography (QCA) or intravascular ultrasound (IVUS); administering an endothelium dependent vasodialator in increasing concentration and determining the changes in coronary blood flow (CBF); measuring changes in forearm blood flow by venous plethysmography before and after administration of vasoactive substances; flow mediated vasodialation of the brachial artery (FMD); and peripheral arterial tonometry (PAT).

As used herein, the term "reversing calcification" includes removing pre-existing calcium deposited in and/or on a blood vessel. Calcification can be detected by any suitable means, including but not limited to thallium stress testing, radiography, coronary calcification scans, fluoroscopy, CT, angioplasty, MRI imaging, sonography, biopsy, by histochemistry or the like.

As used herein, the term "arterial stiffness" refers to the mechanical properties of arteries, including the elasticity (or compliance) of the arteries. Arterial stiffness can be measured by any suitable means, including but not limited to pulse pressure, pulse wave velocity, pulse waveform analysis, and localized assessment of blood vessel mechanics.

As used herein, the term "increasing endothelial nitric oxide production" includes positively affecting nitric oxide production by the endothelium such that a subject's endothelium produces more nitric oxide during and/or after treatment as compared with the endothelial nitric oxide production observed prior to treatment. According to some aspects, increased endothelial nitric oxide production may correspond with increased nitrite plasma concentrations in the subject, which may be a reliable marker of endothelial function.

The following examples are provided as representative of preferred embodiments and are not intended to limit the scope of the present invention.

Example 1

Clinical Study to study the efficacy and safety of Vitamin K2 supplementation on arterial stiffness, the rigidity of arterial walls, in kidney transplantation patients.

A clinical study was carried out. Arterial wall property measurements were taken at t=0 and t=8 weeks and show a dramatic improvement in arterial wall flexibility. This is good support for concluding that the ingestion of vitamin K, even over this short period, is an effective way of improving endothelial function, reducing arterial stiffness and reducing calcification. This is in stark contrast to previous studies (EP 1 728 507) that showed significantly reduced arterial stiffness only after 3 years of ingestion. It is surprising and unexpected because calcification is a slow progressive process and it was thought that reversing this process would also be slow and progressive. This example shows that the preferred treatment period to reverse calcification can be as short as 2 weeks.

Participants were enrolled in a clinical trial in which the effects of vitamin K2 were determined for patients who had recently undergone a kidney transplant. At the beginning of the study, patients were subjected to a non-invasive pulse wave velocity measurement to measure arterial stiffness/flexibility, as well as blood analysis. The study participants were then instructed to receive a specific daily dose of MenaQ7 vitamin K2 menaquinone-7 (360 ug/day) for a total of 8 weeks. At the end of 8 weeks, patients were again examined with a follow-up examination, a non-invasive pulse wave velocity measurement and blood analysis and drug treatment was discontinued.

As part of the blood analysis, carboxylated matrix gla protein (MGP) was measured as a direct measure of vitamin K2 activity. The carboxylated MGP inhibits calcification of blood vessels and Vitamin K2 stimulates carboxylation of MGP. Patients undergoing dialysis exhibit deficiencies of vitamin K2 which may impair carboxylation of the calcification inhibitor matrix gla protein (MGP).

After 8 weeks of treatment, mean reduction in measured pulse-wave velocity was 30%. After 8 weeks of treatment, mean reduction of levels of uncarboxylated MGP was 55%.

Example 2

The effects of low-doses (0.03 mg/kg b.w./day) as well as high-doses (10 mg/kg b.w./day) of vitamin K2 (MK-7), on endothelial function in mice with pre-established atherosclerosis was assessed. The mice were treated with K2 (MK-7) for two months and endothelial function was analyzed in vivo based on functional study (MRI based assessment of NO-dependent vasodilation) as well as by biochemical analysis (plasma nitrate and nitrite concentration). In addition, a comprehensive qualitative and quantitative histological analysis of the effects of K2 (MK-7) on vascular wall structure and atherosclerosis plaque composition was performed.

| Example 2(a): Materials and Methods | |
|---|---|
| Animals | 4-month old ApoE/LDLR-/- mice (n = 76), treated for a two-month period with vitamin K2-MK-7 (menaquinone-7; doses: 0.03 and 10 mg/kg |
| Endpoint assays | Magnetic resonance imaging (MRI)-based assessment of nitric oxide (NO)-dependent vasodilatation in brachiocephalic (BCA) and left common carotid artery (LCA) after acetylcholine (Ach) administration-by MRI 9.4T scanner, total time of measurements: 114 h (1.5 h per animal), acetylcholine (Ach, 16.6 mg/kg b.w.) Nitrite (NO2-) and nitrate (NO3-) concentration in plasma-HPLC-based ENO-20 Plaque size and composition as well as vessel wall area (VWA) in BCA-Histological assessment, cross-section method, BCA cross-sections: total 13000 slides, Photographed: 1214 slides |

Human Contribution 6 Persons Involved in Carrying Out the Experiments and Data Analysis Studies were performed on 4-month old female ApoE/LDLR-/- mice, the model initially described by Ishibashi S, Herz J, Maeda N, Goldstein J, Brown M. *The two-receptor model of lipoprotein clearance: tests of the hypothesis in "knockout" mice lacking the low density lipoprotein receptor, apolipoprotein E, or both proteins.* Proc Natl Acad Sci USA 1994; 10:4431-5, and extensively characterized in previous studies, [see Kostogrys R B, Franczyk-Zarow M, Gasior-Glogowska M, Kus E, Jasztal A, Wrobel T P, et al. *Anti-atherosclerotic effects of pravastatin in brachiocephalic artery in comparison with en face aorta and aortic roots in ApoE/LDLR-/- mice.* Pharmacol Reports 2017; 69:112-8. doi:10.1016/j.pharep.2016.09.014, Tyrankiewicz U, Skorka T, Orzylowska A, Jablonska M, Jasinski K, Jasztal A, et al. *Comprehensive MRI for the detection of subtle alterations in diastolic cardiac function in apoE/LDLR-/- mice with advanced atherosclerosis.* NMR Biomed 2016; 29:833-40. doi:10.1002/nbm.3524, Mateuszuk L, Jasztal A, Maslak E, Gasior-Glogowska M, Baranska M, Sitek B, et al. *Antiatherosclerotic Effects of 1-Methylnicotinamide in Apolipoprotein E/Low-Density Lipoprotein Receptor-Deficient Mice: A Comparison with Nicotinic Acid.* J Pharmacol Exp Ther 2016; 356:514-24. doi:10.1124/jpet.115.228643, Wrobel T P, Marzec K M, Chlopicki S, Maślak E, Jasztal A, Franczyk-Żarów M, et al., *Effects of Low Carbohydrate High Protein (LCHP) diet on atherosclerotic plaque phenotype in ApoE/LDLR-/- mice: FT-IR and Raman imaging.* Sci Rep 2015; 5:14002. doi:10.1038/srep14002, Kostogrys R B, Franczyk-Żarów M, Maślak E, Gajda M, Mateuszuk L, Jackson C L, et al., *Low carbohydrate, high protein diet promotes atherosclerosis in apolipoprotein E/low-density lipoprotein receptor double knockout mice (apoE/LDLR(-/-)).* Atherosclerosis 2012; 223:327-31. doi:10.1016/j.atherosclerosis.2012.05.024, Csányi G, Gajda M, Franczyk-Zarow M, Kostogrys R, Gwoźdź P, Mateuszuk L, et al. *Functional alterations in endothelial NO, PGI2 and EDHF pathways in aorta in ApoE/LDLR-/- mice.* Prostaglandins Other Lipid Mediat 2012; 98:107-15. doi:10.1016/j.prostaglandins.2012.02.002.). Mice were randomly assigned to three experimental groups: control—untreated group and two groups treated for two months with low or high doses of menaquinone-7 (MK-7, 0.03 and 10 mg/kg b.w./day, respectively, given with the food, MK-7 provided by *Pharmaceutical Research* Institute, Warszawa via courtesy of Dr.

Figure 1B:
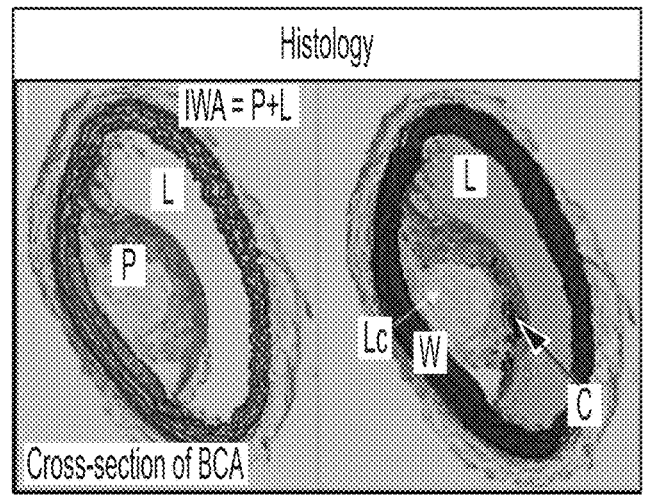
Figure 1C:
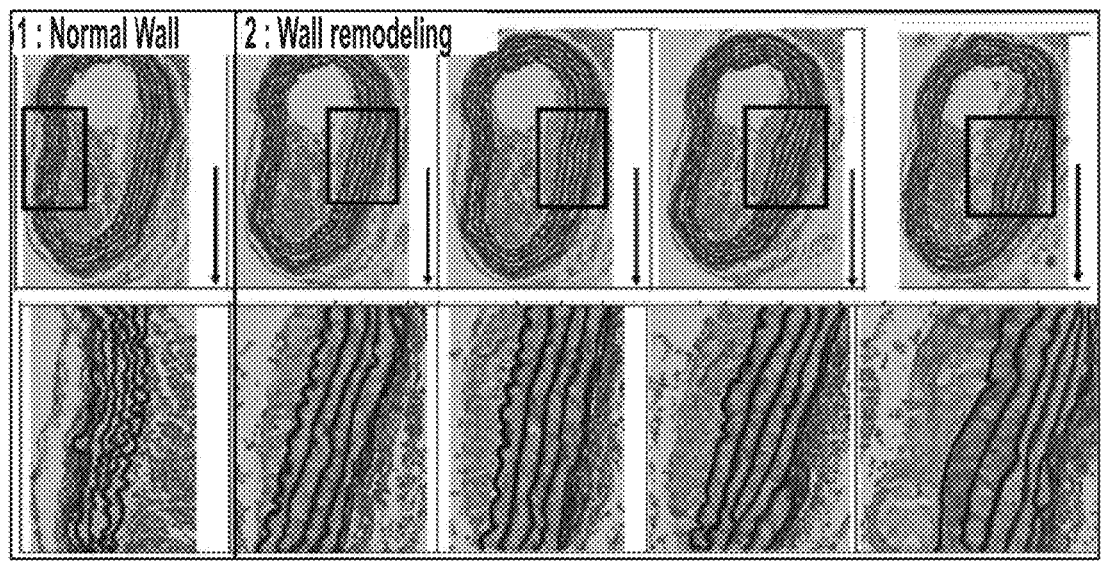

Maresz]. For the assessment of endothelium-dependent vascular responses in vivo 6-month old mice were imaged using MRI-based methods as described previously [See Bar A, Skorka T, Jasinski K, Sternak M, Bartel Ż, Tyrankiewicz U, et al. *Retrospectively-gated MRI for in vivo assessment of endothelium-dependent vasodilatation and endothelial permeability in murine models of endothelial dysfunction.* NMR Biomed 2016; 29(8):1088; Bar A, Skorka T, Jasinski K, Chlopicki S. *MRI-based assessment of endothelial function in mice in vivo.* Pharmacol Reports 2015; 67:765-70. doi: 10.1016/j.pharep.2015.05.007]. During the experiment mice were anaesthetized using isoflurane (1.7 vol %) in an oxygen and air (1:2) mixture. Vasomotor response of the vessels was examined by comparing two, time-resolved 3D images (FIG. 1) of the aortic arch prior to and 25 minutes after intraperitoneal Ach administration (Sigma-Aldrich, Poznań Poland, 50 μl, 16.6 mg/kg b.w.). Images were acquired using the cine IntraGate™ FLASH 3D sequence. End-diastolic volumes of BCA and LCA were analyzed using ImageJ software (1.46r NIH Bethesda, Md., USA) and scripts written in Matlab (MathWorks, Natick, Mass., USA) (FIG. 1A).

After in vivo measurements the mice were injected intraperitoneally with 1000 IU of heparin (Sanofi-Synthelabo; Paris, France) and after 10 min, anesthetized intraperitoneally with 40 mg/kg b.w. of sodium thiopental (Biochemie; Vienna, Austria). Blood samples were collected from heart into test tubes containing additional anticoagulant and centrifuged at 1000 g for 10 min at 4° C. The samples were used for HPLC measurement of nitrate ($NO_3^-$) and nitrite ($NO_2^-$) concentrations in plasma by an ENO-20 NOx Analyzer.

For the determination of atherosclerotic plaque area and composition BCA was dissected, fixed in 4% buffered formalin and embedded in paraffin. 5 μm-thick serial sections of BCA were collected from proximal, middle and distal parts of artery. Originally developed staining with Unna's orcein combined with Martius, Scarlet and Blue trichrome (OMSB), was applied on every tenth section (50 μm interval between each section) for visualization of collagen, elastin, fibrin, red blood cells and vascular smooth muscle cells within atherosclerotic plaque. The areas of particular components of atherosclerotic plaque as well as artery lumen and wall were determined after Columbus-based software processing (FIG. 1B) using a previously developed algorithm [Gajda M, Jasztal A, Banasik T, Jasek-Gajda E, Chlopicki S. *Combined orcein and martius scarlet blue (OMSB) staining for qualitative and quantitative analyses of atherosclerotic plaques in brachiocephalic arteries in apoE/LDLR−/− mice.* Histochem Cell Biol 2017. doi: 10.1007/s00418-017-1538-8.].

Example 2(b): Description of Results

Effects of Treatment with Low and High Dose of Vitamin MK-7 on Endothelium-Dependent Vasomotor Response in ApoE/LDLR−/− Mice In Vivo.

In 6-month old non-treated ApoE/LDLR−/− mice, injection of Ach (16.6 mg/kg b.w. given i.p. in the volume of 50 μl) resulted in constriction of BCA and LCA amounting to −9.13% in BCA and −28.33% in LCA.

A two-month treatment with low doses of vitamin MK-7 was sufficient to improve endothelial function as evidenced by partial reversal of the Ach-induced vasoconstriction response. An increase in volume of BCA (FIG. 2A) and LCA (FIG. 2B) after Ach injection was observed (vessel volume changes: about 3% and ~3%, respectively). Treatment of ApoE/LDLR−/− mice for two months with high doses of vitamin MK-7 also resulted in the improved endothelium-dependent vasodilatation induced by Ach in LCA and BCA. Although the mean results for Ach-induced response in groups treated with low (volume changes: 3.25% and −3.92% for BCA and LCA respectively) and high (volume changes: 3.12% and 4.45% for BCA and LCA respectively) dose of vitamin MK-7 were similar the improvement of endothelial function in the high dose group was more significant due to more homogenous response and lower standard errors.

Figure 3A:
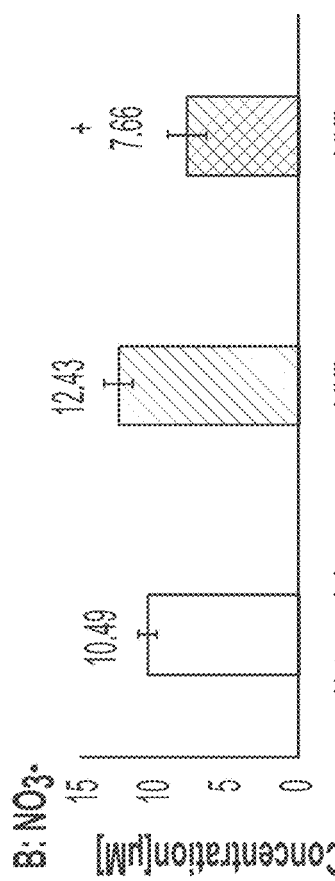
FIG. 3(A)-3(B) show the effects of treatment with low and high dose of vitamin MK-7 on nitrite ($NO_2$-) and nitrate ($NO_3$-) concentration in plasma in ApoE/LDLR-/- mice. Changes in $NO_2$- and $NO_3$- concentration in plasma in non-treated ApoE/LDLR-/- mice (white columns) and in ApoE/LDLR-/- mice treated with vitamin MK-7 given at the low (0.03 mg/kg b.w./day, black columns) or high dose (10 mg/kg b.w./day, columns with diagonal lines) for two months (Untreated_6 m: n=10, MK-7 [0.03 mg/kg]: n=9, MK-7 [10 mg/kg]: n=10). Statistics: one-way ANOVA (HSD Tukey's test); $*p<0.05$, $**p<0.01$ vs. Untreated_6 m mice, $+p<0.05$ for MK-7 [10 mg/kg] vs. MK-7 [0.03 mg/kg].
Figure 3B:
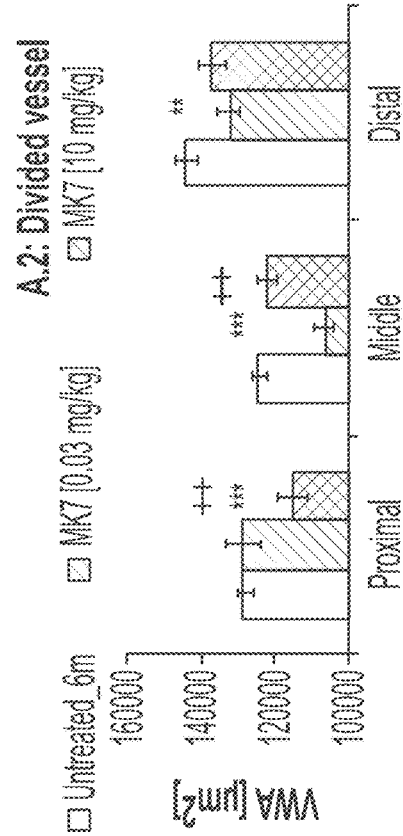

Effects of Treatment with Low and High Dose of Vitamin MK-7 on Plasma Nitrite and Nitrate Concentration Treatment of ApoE/LDLR−/− mice for two months with low as well as high doses of vitamin MK-7 resulted in an increase in $NO_2^-$ concentration (FIG. 3A) in plasma (by about 58% and 42%, respectively). The concentration of $NO_3^-$ (FIG. 3B) in plasma did not change significantly in ApoE/LDLR−/− mice treated with vitamin MK-7 neither in doses of 0.03 mg/kg b.w./day nor 10 mg/kg b.w./day.

Figure 4A:
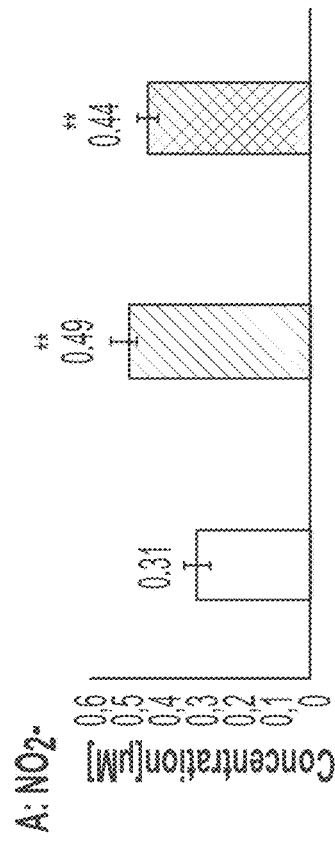
FIG. 4(A)-4(B) show the effects of treatment with low and high doses of vitamin MK-7 treatment on vessel wall structure and media thickness in ApoE/LDLR-/- mice. Vessel wall area (A: VWA) of BCA in non-treated ApoE/ LDLR-/- mice (white columns) and in ApoE/LDLR-/- mice treated with vitamin MK-7 in low (0.03 mg/kg b.w./ day, black columns) and high dose (10 mg/kg b.w./day, columns with diagonal lines) for two months (Untreated_6 m: n=6, MK-7 [0.03 mg/kg]: n=7, MK-7 [10 mg/kg]: n=6). The assessment was performed for entire vessel (A) and for divided vessel (B) in proximal, middle and distal parts. Statistics: Kruskal Wallis test; *p<0.05, p<0.01, *p<0.001 vs. Untreated_6 m mice, +p<0.05, ++p<0.01 for MK-7 [10 mg/kg] vs. MK-7 [0.03 mg/kg].
Figure 4B:
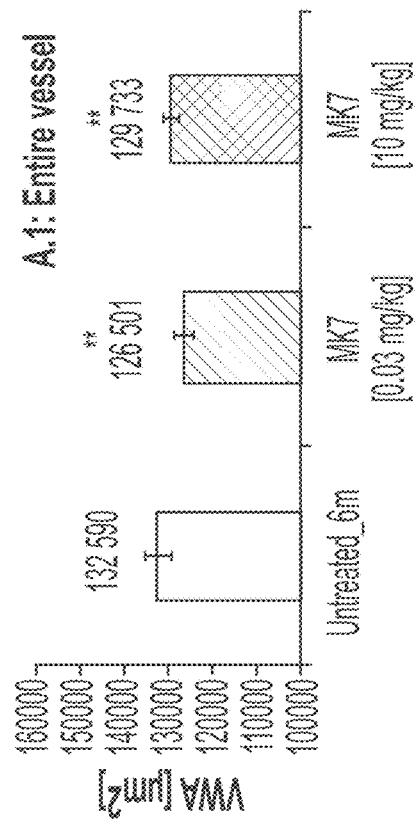
Figure 5D:
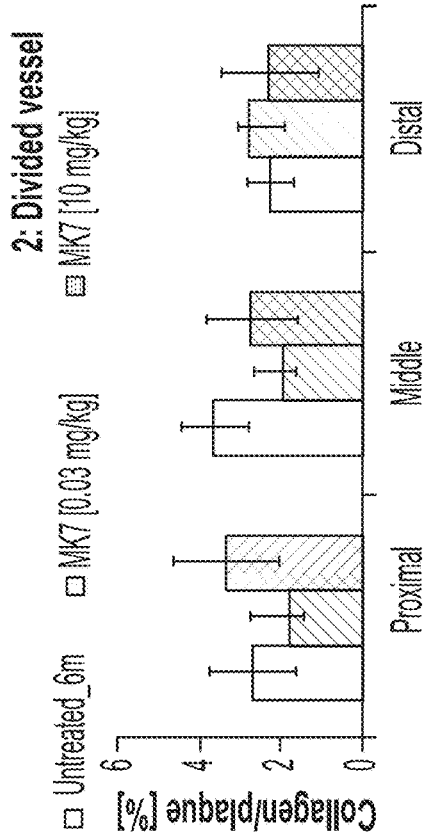
Figure 5D:
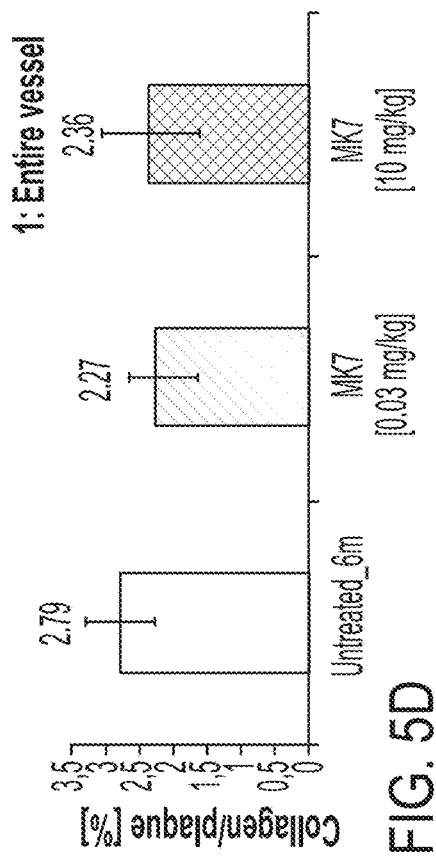
Figure 5E:
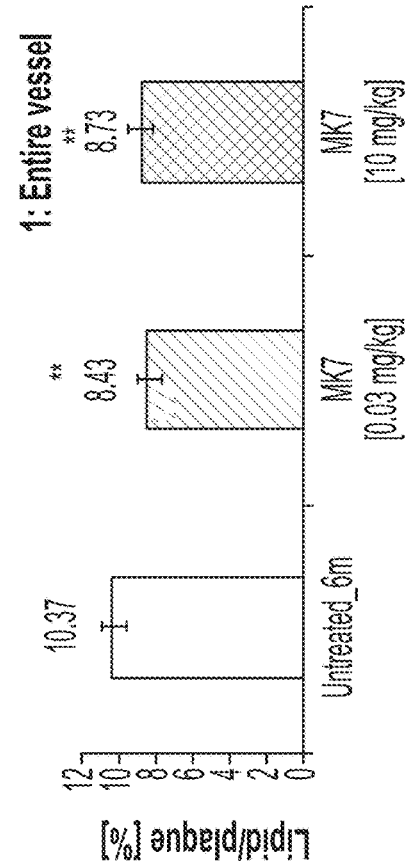

Effects of Treatment with Low and High Dose of Vitamin MK-7 on Vessel Wall Structure and Media Thickness As shown in FIG. 4A treatment with vitamin MK-7 resulted in a clear-cut effect on vessel wall area (VWA), the parameter representative for media layer thickness of the vascular wall. In mice treated for two months with vitamin MK-7, VWA decreased significantly (by about 5%, similarly for low and high dose of vitamin MK-7). Effect was more pronounced in middle and distal part of the vessel in ApoE/LDLR−/− mice treated with lower dose (0.03 mg/kg b.w./day) and in proximal part of the vessel in ApoE/LDLR−/− mice treated with higher dose (10 mg/kg b.w./day) of vitamin MK-7 (FIG. 4B) suggesting stronger effects of low dose of vitamin MK-7 on vascular wall structure in the middle part of the BCA, that part of the BCA characterized by the presence of earliest, least advanced plaques and less advanced vascular pathology.

Effects of Treatment with Low and High Doses of Vitamin MK-7 on Atherosclerotic Plaque Size and Composition Two-month treatment of ApoE/LDLR−/− mice with vitamin MK-7 either low or high doses did not result in a beneficial effect on plaque size. Internal wall area (IWA, FIG. 5A), which is the sum of plaque and lumen areas, decreased only in the middle part of the vessel, in mice treated with lower doses of vitamin MK-7, and this effect was not visible for entire vessel. Consequently, plaque and lumen area expressed as percent of IWA (FIG. 5B-5C) did not change, in mice treated with either low or high doses of vitamin MK-7. However, despite the lack of differences between treated and untreated groups in the content of collagen in plaque (FIG. 5D), significant changes in atherosclerotic plaque composition were observed. In ApoE/LDLR−/− mice treated with low or high dose of vitamin MK-7 lipid core expressed as percent of plaque (FIG. 5E) decreased after two-month treatment either with lower or higher doses of vitamin MK-7 (by about 17%, similarly after low and high dose). Specifically, changes in the content of lipids in plaque were visible in middle part of the BCA with least advanced plaques and the proximal part of the BCA with plaques formed distal to the bifurcation, but not in distal parts with plaques formed proximal to bifurcation.

Example 2(c): Conclusions

In ApoE/LDLR−/− mice with advanced atherosclerosis, treatment with vitamin K2 (MK-7) for two months improved endothelial function in vivo, as evidenced by improvement of functional endothelial-dependent responses induced by acetylcholine in vivo, a well validated measure to assess NO-dependent function [Bar A, Skorka T, Jasinski K, Sternak M, Bartel Ż, Tyrankiewicz U, et al. *Retrospectively-gated MRI for in vivo assessment of endothelium-dependent vasodilatation and endothelial permeability in murine models of endothelial dysfunction*. NMR Biomed 2016; 29(8): 1088] as well as by increased plasma nitrite concentration, the parameter that reflects endothelial NO-dependent function [Kleinbongard P, Dejam A, Lauer T, Rassaf T, Schindler A, Picker O, et al. *Plasma nitrite reflects constitutive nitric oxide synthase activity in mammals*. Free Radic Biol Med 2003; 35:790-6; Kleinbongard P, Dejam A, Lauer T, Jax T, Kerber S, Gharini P, et al. *Plasma nitrite concentrations reflect the degree of endothelial dysfunction in humans*. Free Radic Biol Med 2006; 40:295-302. doi:10.1016/j.freeradbiomed.2005.08.025]. Even low doses of vitamin K2 (0.03 mg/kg b.w./day) had a significant effect. To our knowledge the effects of vitamin K2 on endothelial function has been described here for the first time. Whether the mechanisms of improvement of endothelial function by vitamin K2 are related to canonical or non-canonical mechanisms of action of vitamin K2 requires further mechanistic studies.

The known effect of vitamin K2 on vascular structure was also confirmed, as treatment with vitamin K2 (MK-7) resulted in a significant decrease in media thickness as evidenced by a decrease in vessel wall area. This effect could be linked to known mechanism of vitamin K2-dependent carboxylation of matrix Gla-protein in smooth muscle cells [Schurgers L J, Uitto J, Reutelingsperger C P. *Vitamin K-dependent carboxylation of matrix Gla-protein: a crucial switch to control ectopic mineralization*. Trends Mol Med 2013; 19:217-26. doi:10.1016/j.molmed.2012.12.008], and was the most pronounced in the middle part of the BCA, the part of the vessel with earliest, least advance atherosclerotic plaques.

Although treatment with vitamin K2 (MK-7) did significantly affect the structure of the media layer of the vessel wall, there was no substantial effect of vitamin K2 (MK-7) on the size of the atherosclerotic plaque. These results are not surprising, given the fact that ApoE/LDLR−/− mice with advanced atherosclerosis were used in this study and vitamin K2 was not expected to possess strong anti-atherosclerotic activity. On the other hand, treatment with vitamin K2 (MK-7) substantially changed plaque composition and particularly, the lipid/plaque ratio. The effects of vitamin K2 (MK-7) on plaque composition was the most pronounced in the middle part of the BCA with the earliest atherosclerotic plaques. This result suggests distinct anti-inflammatory effects of vitamin K2 that could translate into pronounced anti-atherosclerotic action if the experiments were carried out in a model with early stages of atherosclerotic plaque development. This result also suggests that treatment with vitamin K2 could have a preventive action on atherosclerotic plaque development.

Altogether, the results presented here provide convincing evidence that apart from its known pharmacological activity on media thickness and other matrix Gla-protein-dependent mechanisms in smooth muscle cells reported previously [Schurgers L J, Uitto J, Reutelingsperger C P. *Vitamin K-dependent carboxylation of matrix Gla-protein: a crucial switch to control ectopic mineralization*. Trends Mol Med 2013; 19:217-26. doi:10.1016/j.molmed.2012.12.008], vitamin K2 improves endothelial function and limits the inflammatory burden of atherosclerotic plaques. The endothelial action of vitamin K2, may be related to K2-dependent carboxylation mechanisms. Whatever is the mechanism, improvement of endothelial function afforded by vitamin K2 may contribute to the improvement of vascular stiffness, that was reported to be improved by vitamin K2 [Knapen M H J, Braam L A J L M, Drummen N E, Bekers O, Hoeks A P G, Vermeer C. *Menaquinone-7 supplementation improves arterial stiffness in healthy postmenopausal women*. Thromb Haemost 2015; 113:1135-44. doi:10.1160/TH14-08-0675]. In fact, vascular stiffness is known to be regulated by endothelial function and improvement of endothelial function improve vascular stiffness [Daiber A, Steven S, Weber A, Shuvaev V V., Muzykantov V R, Laher I, et al. *Targeting vascular (endothelial) dysfunction*. Br J Pharmacol 2016. doi:10.1111/bph.13517; O'Rourke M F, Hashimoto J. *Arterial Stiffness*. J Cardiopulm Rehabil Prev 2008; 28:225-37. doi:10.1097/01.HCR.0000327179.21498.38]. Furthermore, given the fact that the endothelium is involved in most if not all disease states, either as a primary determinant of pathophysiology or as a victim of collateral damage [Chlopicki S. *Perspectives in pharmacology of endothelium: From bench to bedside*. Pharmacol Reports 2015; 67:vi-ix. doi:10.1016/j.pharep.2015.08.005, Frolow M, Drozdz A, Kowalewska A, Nizankowski R, Chlopicki S. *Comprehensive assessment of vascular health in patients; towards endothelium-guided therapy*. Pharmacol Rep 2015; 67:786-92. doi:10.1016/j.pharep.2015.05.010], the finding of the effect of vitamin K2 on endothelial function suggests a novel therapeutic perspective for vitamin K2 as a vasoprotective agent in various diseases/conditions associated with endothelial dysfunction, for example in diabetes, hypertension, atherosclerosis, heart failure, neurodegenerative diseases, kidney transplant patients, hemodialysis patients and many others.

Example 3

In a first part of the study, the effects of low doses (0.05 mg/kg b.w./day) as well as higher doses (0.5 mg/kg b.w./day and 5 mg/kg b.w./day) of vitamin K2 (MK-7, referred to in this example as simply "vitamin K2," unless noted otherwise) on endothelial function in ApoE/LDLR−/−mice without well-established atherosclerotic plaque and with early phase of endothelial dysfunction were assessed.

In a second part of the study, the effects of a low dose (0.03 mg/kg b.w./day) as well as a high doses (10 mg/kg b.w./day) of vitamin K2 (MK-7) on endothelial function in ApoE/LDLR−/−mice with pre-established atherosclerosis were assessed.

In the first part of the study, the mice were treated with vitamin K2 (MK-7) for two, four, or eight weeks. In the second part of the study), the mice were treated with vitamin K2 (MK-7) for eight weeks.

The endothelial function was analyzed in vivo based on functional studies (MRI based assessment and assessment of NO production in aorta using electron paramagnetic resonance) as well as by biochemical analysis (plasma nitrate, nitrite, and vitamin K concentration, and a thrombin generation assessment using a Calibrated Automated Thrombogram). In addition, a comprehensive qualitative and quantitative histological analysis was performed.

Example 3(a): Materials and Methods

In the first part of the study, male mice without well-established atherosclerotic plaques and with early phase of endothelial dysfunction (8-11 weeks of age) were used to examine the effects of two-, four-, and eight-week treatments with a low dose (0.05 mg/kg b.w./day) or higher doses (0.5 and 5 mg/kg b.w./day) of vitamin K2 (MK-7). Mice were randomly assigned to one of four experimental groups:

control (untreated group) and three groups treated with vitamin K2 at a dose of 0.05, 0.5, and 5 mg/kg b.w./day, respectively. End-point measurements were performed at the age of 10-16 weeks.

In the second part of the study, female mice with advanced endothelial dysfunction and pre-established atherosclerosis (16 weeks of age) were treated with K2 (MK-7) for 8 weeks. In this part of the study, mice were randomly assigned to one of three experimental groups: control (untreated group) and two groups treated with low and high doses (0.03 and 10 mg/kg b.w./day, respectively). End-point measurements were performed at the age of 24 weeks.

To perform both studies, vitamin K2 was dissolved in soybean oil and administrated as a part of a semi-synthetic AIN 93G diet as shown in Table 1, without or with a standard vitamin mixture containing vitamin K1.

Mice were housed in collective cages in a room with constant environmental conditions (22-25° C., 65-75% humidity, and 12 hour light/dark cycle). Animals had ad libitum access to daily provided diets and water.

TABLE 1

| | Untreated female | Untreated male | Dose of K2 - MK-7 [mg/kg] | | | | |
|---|---|---|---|---|---|---|---|
| | | | 0.03 | 0.05 | 0.5 | 5 | 10 |
| Corn starch [g] | | | 533 | | | | |
| Caseine [g] | | | 200 | | | | |
| Sucrose [g] | | | 100 | | | | |
| Soybean oil [g] | | | 70 | | | | |
| Cellulose powder | | | 50 | | | | |
| Mineral mixture [g] | | | 35 | | | | |
| Vitamin mixture 1[1] [g] | 10 | — | — | — | — | — | — |
| Vitamin mixture 2[2] [g] | — | 10 | 10 | 10 | 10 | 10 | 10 |
| Choline bitartrate | | | 2.5 | | | | |
| t-butylohydroquinone | | | 0.014 | | | | |
| Vitamin MK-7 in diet [mg] | — | — | 0.15 | 0.25 | 2.50 | 25.00 | 50.00 |
| Equivalent dose of MK-7 [mg/kg b.w.] | — | — | 0.03 | 0.05 | 0.50 | 5.00 | 10.00 |

[1]standard vitamin mixture containing 75 mg/kg (equivalent to dose 0.15 mg/kg b.w./day) yitamin K1
[2]vitamin mixture without vitamin K1

Assessment of Endothelium-Dependent Vasodilatation In Vivo by Magnetic Resonance Imaging (MRI)

Magnetic resonance imaging (MRI) experiments were performed using a 9.4T scanner (BioSpec 94/20 USR, Bruker, Germany) located in the Department of Magnetic Resonance Imaging, Institute of Nuclear Physics, Polish Academy of Sciences in Krakow. During the experiment, mice were anaesthetized using isoflurane (Aerrane, Baxter Sp. z o. o., Poland, 1.7 vol %) in an oxygen and air (1:2) mixture and imaged in the supine position. Activity of the heart, respiration, and body temperature (maintained at 37° C. using circulating warm water) were monitored using a Monitoring and Gating System (SA Inc., Stony Brook, N.Y., USA).

Endothelial function was assessed based on vascular responses to acetylcholine (Ach) administration in brachiocephalic artery (BCA), left common carotid artery (LCA) (FIGS. 6 A and B) and abdominal aorta (AA) (FIG. 6C) as well as to responses to increase in flow (flow-mediated dilatation, FMD) in femoral artery (FA) (FIG. 6D) as described in Bar A, Skorka T, Jasinski K, Sternak M, Bartel Ż, Tyrankiewicz U, et al. Retrospectively-gated MRI for in vivo assessment of endothelium-dependent vasodilatation and endothelial permeability in murine models of endothelial dysfunction. NMR Biomed 2016; 29(8):1088; Sternak M, Bar A, Adamski M G, Mohaissen T, Marczyk B, Kieronska A, et al. The Deletion of Endothelial Sodium Channel α (αENaC) Impairs Endothelium-Dependent Vasodilation and Endothelial Barrier Integrity in Endotoxemia in Vivo. Front Pharmacol 2018; 9:178. doi:10.3389/fphar.2018.00178; and Bar A, Olkowicz M, Tyrankiewicz U, Kus E, Jasinski K, Smolenski R T, et al. Functional and Biochemical Endothelial Profiling In Vivo in a Murine Model of Endothelial Dysfunction; Comparison of Effects of 1-Methylnicotinamide and Angiotensin-converting Enzyme Inhibitor. Front Pharmacol 2017; 8:183. doi:10.3389/fphar.2017.00183).

Vasomotor response was examined by comparing two time-resolved 3D images of the vessels prior to and 25 minutes after intraperitoneal Ach administration (Sigma-Aldrich, Poznan Poland: 50 μl, 16.6 mg/kg), as well as prior to and 5 minutes after vessel occlusion. Images were acquired using the cine IntraGate™ FLASH 3D sequence, reconstructed with the IntraGate 1.2.b.2 macro (Bruker). End-diastolic volumes of vessels were analyzed using ImageJ software 1.46r (NIH Bethesda, Md., USA) and scripts written in Matlab (MathWorks, Natick, Mass., USA). Imaging parameters included the following: repetition time (TR)—6.4 ms, echo time (TE)—1.4 ms, field of view (FOV)—30×30×5 mm3, matrix size—256×256×30, flip angle (FA)—30°, and number of accumulations (NA)—15, reconstructed to 7 cardiac frames. Total scan time was 10 minutes.

Assessment of Endothelial NO Production in Aorta Using Electron Paramagnetic Resonance For measurements of endothelial nitric oxide synthase (eNOS)-dependent nitric oxide (NO) production, EPR spin-trapping with diethyldithiocarbamic acid sodium salt (DETC) was used ex vivo, as described in Przyborowski K, Proniewski B, Czarny J, Smeda M, Sitek B, Zakrzewska A, et al. Vascular Nitric Oxide-Superoxide Balance and Thrombus Formation after Acute Exercise. Med Sci Sport Exerc 2018:1. doi:10.1249/MSS.0000000000001589, with minor modifications. Isolated aorta cleared from surrounding tissue was opened longitudinally and preincubated with 10 μM L-NIL (N6-(1-Iminoethyl)-lysine, hydrochloride) in Krebs-HEPES buffer for 30 minutes at 37° C. in a well of a 48-well plate. Next, 250 μL of Fe(DETC)2 colloid was added and aorta was stimulated with calcium ionophore A23187 (the final concentration was 1 μM) and subsequently, incubated for 90 minutes at 37° C. Finally, aorta was weighed and frozen in liquid nitrogen (suspended in fresh buffer) into the middle of a 400 μL column of Krebs-Hepes buffer and stored at −80° C. until measured. EPR spectra were obtained using an X-band EPR spectrometer (EMX Plus, Bruker, Germany), equipped with a rectangular resonator cavity H102. Signals were quantified by measuring the total amplitude of the NO—Fe(DETC)2 after correction of baseline. The quantitative results of NO production assessed by EPR were expressed in AU/mg of tissue.

Blood Sampling and Biochemical Analysis

After in vivo MRI measurements the mice were injected intraperitoneally with 1000 IU of heparin (Sanofi-Synthelabo; Paris, France) and after 15 minutes, anesthetized intraperitoneally with 100 mg/kg b.w ketamine+10 mg/kg b.w xylazine mg/kg b.w. Blood samples were collected from the heart into test tubes containing additional anticoagulant. On the same day, 25 μL of whole blood was used for blood count analysis, using automatic biochemistry analyzer ABX Pentra 400 (Horiba Medical, Kyoto, Japan). Remaining blood was centrifuged at 1000 g for 10 minutes in 4° C. and plasma was deep frozen for HPLC measurement of nitrate ($NO^{3-}$) and nitrite ($NO^{2-}$) concentrations by ENO-20 NOx Analyser, or for lipid profile and liver enzyme analysis by biochemical analyzer (ABX Pentra 400—Horiba Medical, Kyoto, Japan). Moreover, L-APCI-MS/MS-based assessment of vitamin K derivatives concentration was performed as described below in plasma samples obtained from blood samples collected with EDTA K2 and Protease Inhibitor Cocktail that were centrifuged at 1000 g for 10 minutes in 4° C.

LC-APCI-MS/MS Based Assessment of Plasma Concentration of Vitamin K

To measure concentration of vitamin K2 and also other vitamin K derivatives (i.e., vitamin K1—phylloquinone (PK) and MK-4) in plasma, a selective and sensitive method based on high performance liquid chromatography-tandem mass spectrometry with atmospheric pressure chemical ionization technique (LC-APCI-MS/MS) was developed. The methodology was based on Riphagen I J, van der Molen J C, van Faassen M, Navis G, de Borst M H, Muskiet F A J, et al. Measurement of plasma vitamin K1 (phylloquinone) and K2 (menaquinones-4 and -7) using HPLC-tandem mass spectrometry. Clin Chem Lab Med 2016; 54:1201-10. doi: 10.1515/cclm-2015-0864, with some adjustments.

An individual stock solution of analytes (K1, MK-4, and MK-7) and internal standard (K1-d7) of 100 μg/mL were prepared by dissolving the 1 mg of standards in 10 mL of ethanol. A standard mixture stock solution of 10 μg/mL was prepared in ethanol. The individual stock solutions and standard mix were stored in dark at −20° C. prior to use. For the analytical curves, working solutions of standard mixture ranging from 0.5 ng/mL to 10 μg/mL were prepared by dilution of stock solution with ethanol. The internal standard working solution of 1 μg/mL was prepared by diluting K1-d7 stock solution with ethanol. A calibration curve samples were prepared by mixing 90 μL of blank plasma samples with 10 μL of appropriate standard working solution mixture. The concentration of calibration points were equivalent to 0.05; 0.1; 0.25; 0.5; 0.75; 1; 2.5; 5; 10; 25; 50; 100; 200; 400; 600; 750; 1000 ng/mL.

An aliquot of 100 μL of plasma in amber tubes was spiked with 10 μL of internal standard—vitamin K1-d7 (1 ug/mL in ethanol). Extra ethanol (200 μL) was added to denature the protein, briefly mixed and 1 mL of hexane, followed by shaking for 15 minutes. The solution was centrifuged at 15.000 rpm for 15 minutes, and the upper layer was quantitatively transferred to a new tube and evaporated under the stream of nitrogen at room temperature. The residue was dissolved with 30 μL of 2-propanol, centrifuged at 15.000 rpm for 15 minutes, and 5 μL was injected into the column.

The HPLC analysis was conducted with an Ultimate 3000 HPLC system (Dionex, Sunnyvale, Calif., US). Separations were carried out using a reversed-phase PFP analytical column (Kinetex 2.6 μm PFP, 100 Å, 100.0×3.0 mm, Phenomenex, Torrance, Calif., US) with a mobile phase consisted of 0.1% of formic acid in 2-propanol (phase A) and 0.1% formic acid in 5 mM ammonium formate (phase B) in gradient elution. The chromatogram of determined vitamin K derivatives is shown in FIG. 12.

Mass spectrometry was performed with a TSQ Quantum Ultra triple quadrupole mass spectrometer (Thermo Scientific, Waltham, Mass., US), equipped with APCI electrospray ion source. All MS analysis were collected in positive ionisation mode. The working parameters of mass spectrometer were as follows: corona discharge needle voltage, 4 kV, vaporiser temperature: 325° C., sheath gas pressure 50 Arb, ion sweep gas pressure 10 Arb, auxiliary gas pressure 30 Arb, capillary temperature 325° C. and collision pressure 1.5 mTorr with Argon as a collision gas.

Thrombin Generation Assessment Using Calibrated Automated Thrombogram (CAT)

Thrombin generation was measured in platelet-poor mice plasma using calibrated automated thrombography (CAT) technique as described in Hemker H C, Giesen P, Al Dieri R, Regnault V, de Smedt E, Wagenvoord R, et al. Calibrated automated thrombin generation measurement in clotting plasma. Pathophysiol Haemost Thromb 2003; 33:4-15. doi: 71636. Thrombin generation was activated by mixing 21 μL of diluted plasma (1:1 with BSA5 buffer) with 7 μL of fluorogenic substrate (Z-Gly-Gly-Arg-AMC, 16.6 mM) and 14 μL of trigger solution containing phospholipids, tissue factor and $CaCl_2$ (4 μM, 1 pM and 16.6 mM, respectively). In the calibration wells, the 14 μL of reagents were replaced with calibrator (102 nM). Immediately after the activation, 5 μL of the mixture was pipetted on paper disks in a flat bottom 96-well polystyrene plate and covered with 40 μL of mineral oil. Fluorescent signals were measured using the Fluoroskan Ascent software (Thermo Labsystems, Helsinki, Finland) and transformed into thrombin concentration as described in Hemker H C, Kremers R. Data management in Thrombin Generation. Thromb Res 2013; 131:3-11. doi: 10.1016/j.thromres.2012.10.011. The parameters analyzed included endogenous thrombin potential (ETP), peak thrombin concentration (peak), and lag time.

Histological Assessment of Area and Composition of Atherosclerotic Plaque (Cross-Section Method)

For the determination of atherosclerotic plaque area and composition isolated brachiocephalic artery (BCA) was dissected, fixed in 4% buffered formalin, and embedded in paraffin. 5 μm-thick serial sections of BCA were collected from the proximal to distal part of the artery. Staining with Unna's orcein combined with Martius, Scarlet and Blue trichrome (OMSB) was applied on every tenth section (50 μm interval between each section) for quantitative analysis of atherosclerotic plaques. The areas of particular components of atherosclerotic plaque as well as artery lumen and wall were determined after Columbus-based software processing (FIG. 9) using specially-designed algorithm as described in Gajda M, Jasztal A, Banasik T, Jasek-Gajda E, Chlopicki S. Combined orcein and martius scarlet blue (OMSB) staining for qualitative and quantitative analyses of atherosclerotic plaques in brachiocephalic arteries in apoE/LDLR−/− mice. Histochem Cell Biol 2017. doi:10.1007/s00418-017-1538-8. The parameters analyzed include vessel wall area (VWA), internal vessel area (IVA=plaque area+lumen area), plaque area (expressed as percent of internal wall area: plaque/IWA), and lumen area (expressed as percent of internal wall area: lumen/IWA).

Immunohistochemical Detection of Macrophages in Atherosclerotic Plaque in BCA

For detection of macrophages in BCA, atherosclerotic plaque immunohistochemical staining was performed. After heat-induce epitope retrieval, with 10 mM sodium citrate buffer (pH 6), deparaffinised sections were blocked with 5% normal goat serum and 1% hydrogen peroxide. Macrophages were revealed by overnight incubation with monoclonal anti-Mac-3 antibody (BD Pharmingen, 550292). Next, sections were treated with biotinylated secondary antibody, followed by horseradish peroxidase-conjugated streptavidin. 3,3'-diaminobenzidine (DAB) as a chromogen was used for visualization of antibody-antigen interaction. Sections were counterstained with hematoxylin. Intensity of Mac-3 staining was estimated manually considering quantity and intensity of positive reactions. Final results are shown as a mean from two independent analysis.

Example 3(b): Description of Results

Effects of Vitamin K2 Treatment on Nitric Oxide-Dependent Endothelial Function in Young ApoE/LDLR−/− Mice at the Stage Prior to Advanced Atherosclerotic Plaque Development As shown in FIG. 7(A-B), the four-week treatment with low dose (0.05 mg/kg b.w./day) of vitamin K2 (MK-7) improved FMD in FA (volume changes: 33.26% in mice treated with K2 and 17.45% in untreated mice, p<0.001) as well as improved Ach response in AA (volume changes: −1.59% in mice treated with K2 and −11.22% in untreated mice, p=0.02) in 15-week-old treated ApoE/LDLR$^{-/-}$ mice as compared with untreated ApoE/LDLR$^{-/-}$ mice. At this age, ApoE/LDLR$^{-/-}$ mice are characterized by full-blown phenotype of endothelial dysfunction but not yet advanced atherosclerosis plaques.

Figure 7A:
Figure 7A:
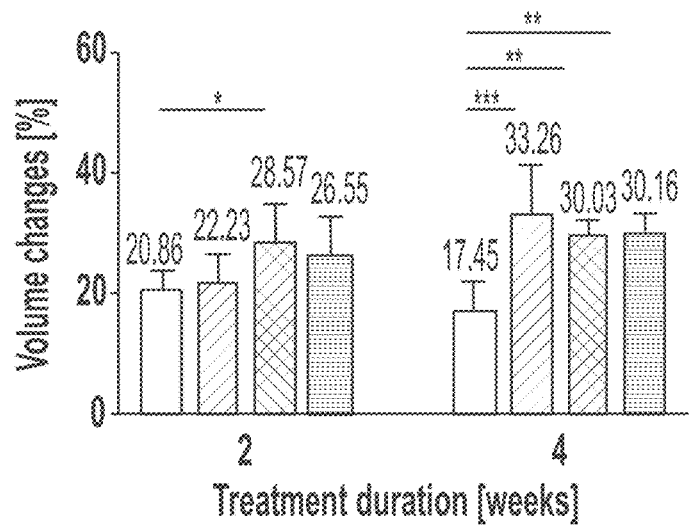
Figure 7B:
Figure 7B:
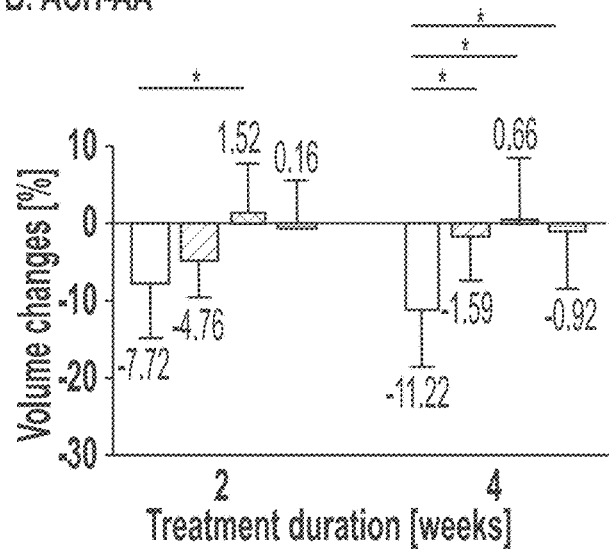
Figure 7C:
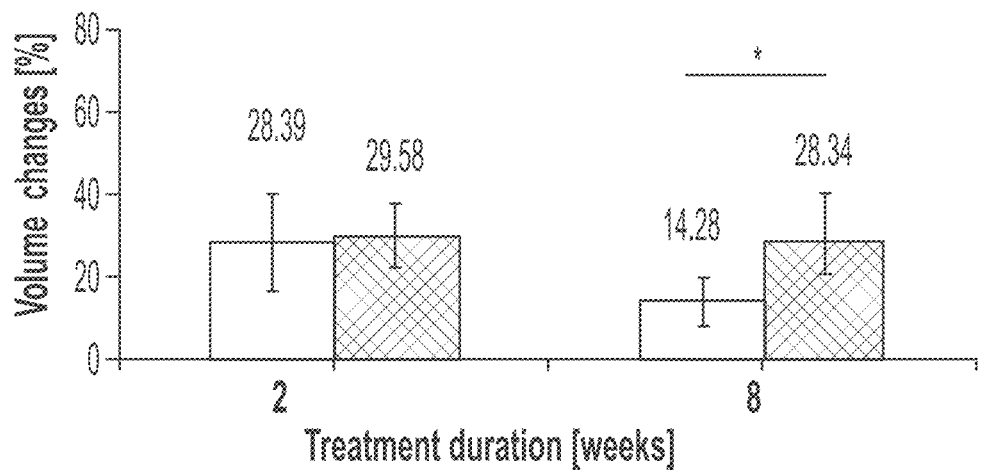
Figure 7D:
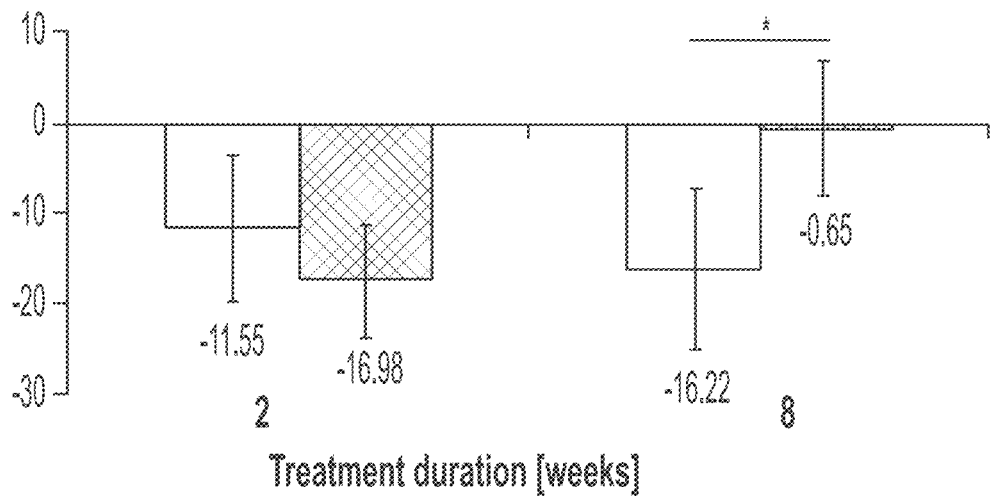
Figure 7E:
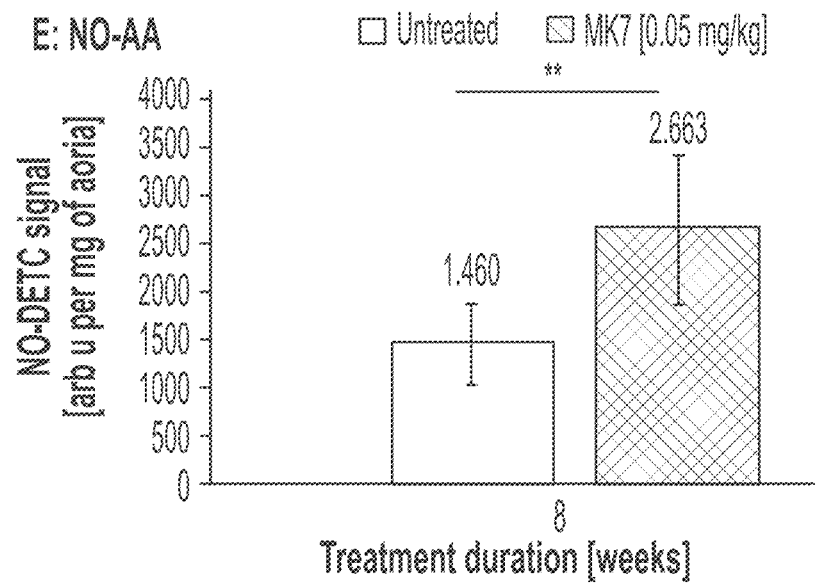

In contrast to the four-week period of vitamin K2 treatment, the two-week period of treatment with low dose of vitamin K2 (0.05 mg/kg b.w./day) was not sufficient to improve endothelial function, as evidenced by the lack of changes in the magnitude of vasodilatation in response to increase in flow in femoral artery (FMD-FA, FIG. 7A) and in the magnitude of endothelium-dependent response to acetylcholine in abdominal aorta (ACH-AA, FIG. 7B). However, higher doses of vitamin K2 improved endothelial function just after two weeks of treatment (volume changes: 28.57% in FA, p=0.04 and 1.52% in AA, p=0.05 for the dose of 0.5 mg/kg b.w./day and volume changes: 26.55% in FA, p=0.1 and 0.16% in AA, p=0.1 for the dose of 5 mg/kg b.w./day as compared with 20.86% in FA and −7.72% in AA in untreated mice, respectively).

Figure 8A:
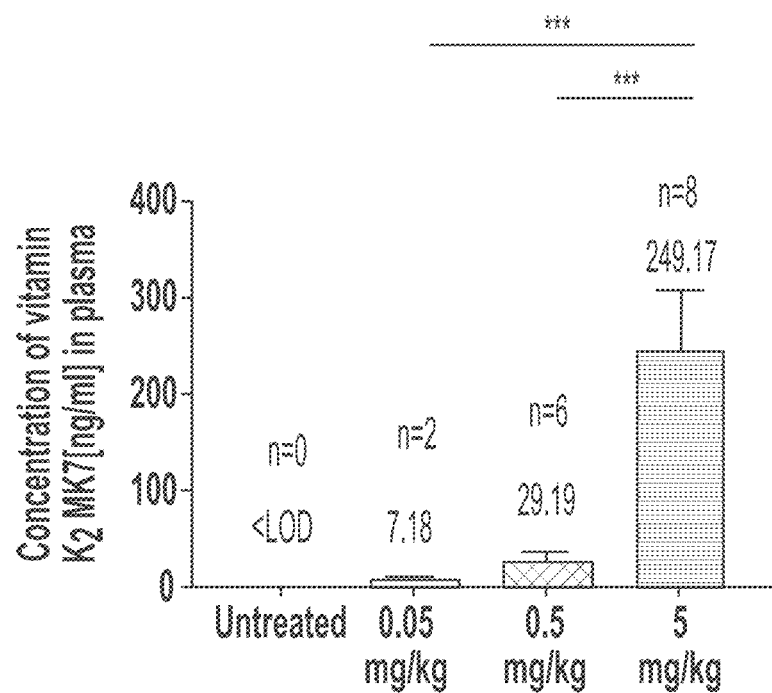
Figure 8B:
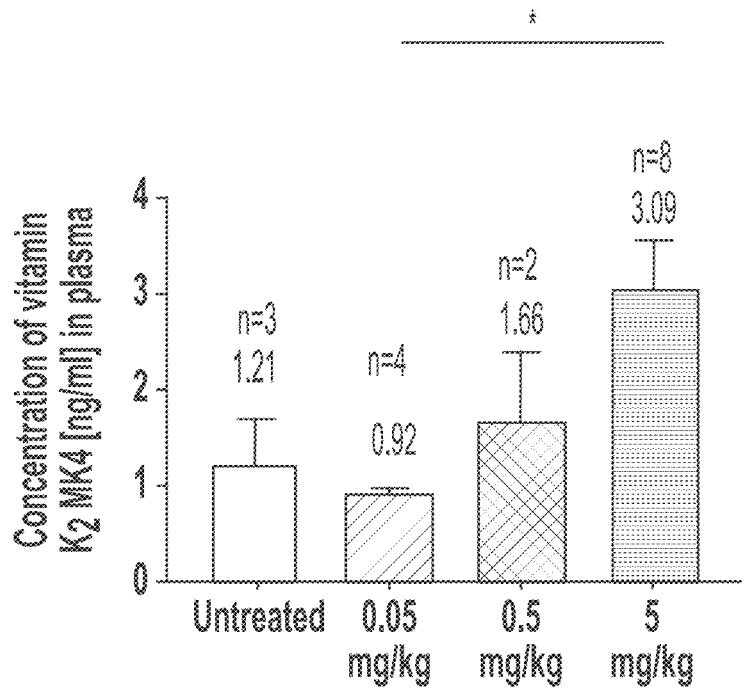
Figure 8C:
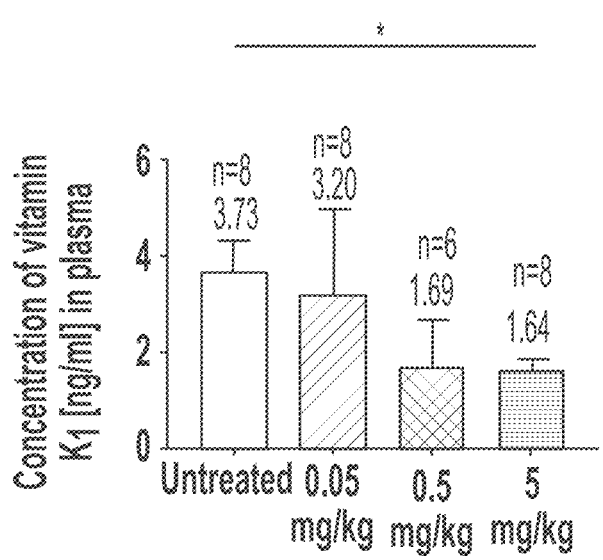
Figure 8D:
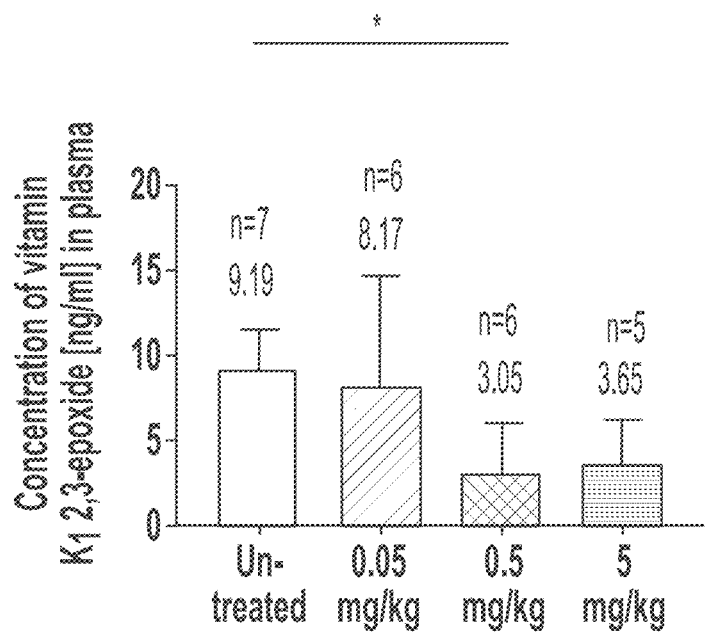
Figure 8E:
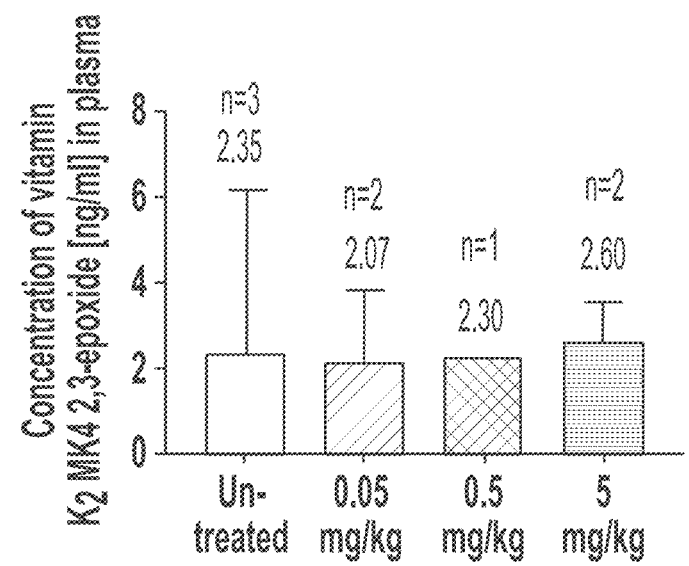

The improvement in endothelial function afforded by four weeks of treatment with higher doses of K2 (0.5 mg/kg b.w./day and 5 mg/kg b.w./day) was not superior as compared with that achieved by low dose treatment with K2 administered for 4 weeks (FIG. 7(A-B)), despite the fact, that three doses of vitamin K2 (0.05; 0.5; 5 mg/kg b.w./day) resulted in a dose-dependent increase in plasma concentration of K2 (FIG. 8A) and MK-4 (FIG. 8B). Concentration of MK4 2,3-epoxide (FIG. 8E) in plasma was maintained at similar level in all groups, while vitamin K1 (FIG. 8C) and K1 2,3-epoxide (FIG. 8D) plasma concentration tent to decrease with increasing dose of vitamin K2.

Moreover, prolongation of the treatment time to eight weeks (FIG. 7C-D) was also not associated with superior effect of treatment as compared with K2 administered at low dose (0.05 mg/kg b.w./day) (volume changes: 28.34% in FA, p=0.03 and −0.65% in AA, p=0.05 as compared with 14.28% in FA and −16.22% in AA in untreated mice, respectively).

The positive effects of low dose of vitamin K2 (0.05 mg/kg) improving the endothelium-dependent vasodilation measured in vivo was confirmed by showing increased nitric oxide production measured in the same animals by EPR in ex vivo aorta, taken from ApoE/LDLR$^{-/-}$ mice treated with low dose (0.05 mg/kg b.w./day) of vitamin K2 (FIG. 2E) as compared with untreated, age-matched ApoE/LDLR$^{-/-}$ mice.

Effects of Vitamin K2 Treatment on Endothelial Function in Older ApoE/LDLR$^{-/-}$ Mice at the Stage of Advanced Atherosclerosis In 24-week-old, non-treated ApoE/LDLR$^{-/-}$ mice, characterized by advanced endothelial dysfunction and presence of atherosclerotic plaques, injection of Ach resulted in constriction of BCA and LCA amounting to −9.13% in BCA and −28.33% in LCA. As shown in FIG. 10(A-B), eight-week treatment with low dose of vitamin K2 (0.03 mg/kg b.w/day) resulted in improvement of endothelial function as evidenced by partial reversal of Ach-induced vasoconstriction response. A change in volume of BCA (FIG. 10A) and LCA (FIG. 10B) after Ach injection was about 3% and −3%, respectively. Treatment of ApoE/LDLR$^{-/-}$ mice for eight weeks with high dose (10 mg/kg b.w/day) of vitamin K2 also resulted in the improved endothelium-dependent vasodilatation induced by Ach in LCA and BCA. The mean results for Ach-induced response in groups treated with low (volume changes: 3.25% and −3.92% for BCA and LCA respectively) and high (volume changes: 3.12% and 4.45% for BCA and LCA respectively) dose of vitamin K2 was similar. However, the improvement of endothelial function in high dose group was more significant due to more homogenous response and lower standard errors.

Improvement of endothelium-dependent vasodilation by treatment of older ApoE/LDLR$^{-/-}$ mice for eight weeks with low as well as high dose of vitamin K2 resulted in increase in $NO_2^-$ concentration (FIG. 10O) in plasma (by about 58% and 42%, respectively). Concentration of $NO_3^-$ (FIG. 10D) in plasma did not change significantly in ApoE/LDLR$^{-/-}$ mice treated with vitamin K2 neither at a dose of 0.03 mg/kg b.w./day nor at a dose of 10 mg/kg b.w./day.

Eight-week treatment of ApoE/LDLR$^{-/-}$ mice with vitamin K2 of either dose did not affect lipid profile, liver enzymes concentration, blood cell count (Table 2) or thrombin generation (FIG. 10(E-F)).

TABLE 2

|  | Untreated mice | MK-7 0.03 mg/kg | MK-7 10 mg/kg |
|---|---|---|---|
| Lipid profile: | | | |
| TC (mmol/L) | 15.96 ± 4.21 | 19.96 ± 3.82 | 16.59 ± 2.89 |
| Triglycerides (mmol/L) | 1.24 ± 0.57 | 2.15 ± 0.46 | 1.87 ± 0.98 |
| Liver enzymes: | | | |
| ALT (U/L) | 46.26 ± 17.97 | 45.20 ± 15.72 | 47.58 ± 19.55 |
| AST (U/L) | 108.48 ± 24.97 | 97.99 ± 27.89 | 74.40 ± 20.44 |
| SAA (µg/ml) | 35.92 ± 4.48 | 34.23 ± 10.42 | 36.63 ± 8.06 |
| Blood count: | | | |
| GRA | 0.64 ± 0.13 | 0.73 ± 0.24 | 0.52 ± 0.22 |
| GRA (%) | 16.78 ± 2.89 | 16.00 ± 6.36 | 14.08 ± 3.73 |
| Hematocrit | 45.57 ± 1.26 | 49.99 ± 9.02 | 44.07 ± 7.50 |
| HGB | 12.61 ± 1.29 | 13.81 ± 2.53 | 12.09 ± 1.77 |
| LYM | 2.15 ± 0.58 | 3.10 ± 1.93 | 1.6 ± 1.25 |
| LYM (%) | 74.27 ± 4.66 | 75.45 ± 10.25 | 77.39 ± 4.50 |
| MCH | 14.85 ± 0.66 | 15.13 ± 0.38 | 14.57 ± 0.18 |
| MCHC | 27.74 ± 1.36 | 28.05 ± 0.39 | 27.22 ± 0.59 |
| MCV | 53.50 ± 1.00 | 54.00 ± 2.00 | 53.00 ± 1.00 |
| MON | 0.25 ± 0.10 | 0.30 ± 0.05 | 0.15 ± 0.20 |
| MON (%) | 8.95 ± 2.10 | 8.55 ± 2.00 | 8.53 ± 1.43 |
| MPV | 5.01 ± 0.19 | 5.20 ± 0.33 | 4.97 ± 0.19 |
| PLT | 726.50 ± 108.25 | 696.50 ± 154.38 | 727.02 ± 127.25 |
| Erythrocytes | 8.49 ± 0.37 | 9.37 ± 1.32 | 8.30 ± 1.21 |
| RDW | 12.50 ± 0.37 | 12.27 ± 0.39 | 12.13 ± 0.15 |
| Leukocytes | 3.05 ± 0.60 | 4.25 ± 1.61 | 2.23 ± 1.77 |

Effects of Treatment with Vitamin K2-MK-7 on Vessel Wall Structure, Media Thickness, and Atherosclerotic Plaques Size in Brachiocephalic Artery in Older ApoE/LDLR-/- at the Stage of Advanced Atherosclerosis As shown in FIG. 11A, in 24-week-old ApoE/LDLR-/- mice treated for eight weeks with vitamin K2 (MK-7), there was an clear-cut effect on vessel wall area (VWA), the parameter representative for media layer thickness of the vascular wall as compared with 24-week-old non-treated ApoE/LDLR-/- mice. The effects of low and high dose of vitamin K2 was similar in magnitude (VWA decreased by about 5% for low and high dose of vitamin K2-MK-7).

The plaque size in 24-week-old ApoE/LDLR-/- mice treated with vitamin K2 for eight weeks with vitamin K2 either at low (0.03 mg/kg b.w./day) or at high dose (10 mg/kg b.w./day) was not different as compared with non-treated 24-week-old ApoE/LDLR-/-mice. Internal wall area (IWA, FIG. 11(B)), which is the sum of plaque and lumen areas, decreased only in the middle part of the vessel, in mice treated with lower dose of vitamin K2 (data not shown), but this effect was not visible for entire vessel. Consequently, plaque and lumen area expressed as percent of IWA (FIG. 11(C-D)) did not change in mice treated with either low or high dose of vitamin K2. Lack of the effects of vitamin K2 on atherosclerotic plaque size was compatible with unchanged expression of MAC in atherosclerotic plaques, suggesting similar macrophage contents of the atherosclerotic plaques in treated and non-treated 24-month-old ApoE/LDLR-/- mice (Intensity of MAC-3 staining: 92±28 in untreated mice; 128±26 in mice treated with K2-MK-7 in low dose (0.05 mg/kg b.w./day); 139±29 in mice treated with K2-MK-7 in high dose (10 mg/kg b.w./day)).

Example 3(c): Conclusions

It was concluded that vitamin K2 (MK-7) improves NO-dependent endothelial function in ApoE/LDLR$^{-/-}$ mice. In particular, the results show that vitamin K2 affords a vasoprotective effect independently of whether endothelial dysfunction was treated with vitamin K2 prior to or concurrently with the occurrence of atherosclerotic plaques in ApoE/LDLR$^{-/-}$ mice, suggesting that vitamin K2 induced an effect on endothelial function that is not linked to a possible anti-atherosclerotic effect of vitamin K2. Furthermore, these results did not confirm any significant effect of vitamin K2 (MK-7) treatment on atherosclerotic plaque size and macrophages content. Vitamin K2-induced improvement of endothelial function was also not linked to changes in activity of coagulation factors, as evidence by unchanged thrombin activity (CAT). It was thus concluded that a low dose of vitamin K2 (MK-7), especially those comparable with effective doses of vitamin K2 recommended for humans to provide benefits for cardiovascular health, may play an important role in the regulation of endothelial function.

This study shows that a low dose of vitamin K2 (MK-7) may improve endothelial-dependent responses induced by acetylcholine in aorta and induced by flow in femoral aorta. These responses were shown previously to be mediated by endothelial NO in mice. The improvement of endothelial function by treatment with vitamin K2 was confirmed ex vivo by EPR measurements in aorta, which showed increased NO production in aorta taken from vitamin K2-treated ApoE/LDLR$^{-/-}$ mice as compared with non-treated animals. The improvement of endothelium dependent vasodilation by vitamin K2 also correlated with increased nitrite plasma concentration, a reliable marker of endothelial function.

The treatment with a low dose of vitamin K2 (0.05 mg/kg b.w./day) resulted in barely detectable levels of MK-7 in plasma (detected in two per six mice, amounting to 11.06 nM), suggesting that MK-7 is endowed with pharmacological efficacy to improve endothelial function in the nanomolar range of concentrations. Interestingly, the endothelial effects of vitamin K2 after four weeks of treatment could be accelerated to two weeks of treatment, but not enforced by treatment with higher doses of vitamin K2 (0.5, 5 mg/kg b.w./day), despite higher plasma concentration of MK-7 as well as the parallel increase in plasma concentrations of MK-4 that was achieved by higher doses of vitamin K2 treatment regimens. These results seem compatible with the notion that vitamin K2-MK-7 is converted in vivo to vitamin K2-MK-4 via UBIAD1, but whether the endothelial effect reported here was induced directly by MK-7 or by MK-4 after MK-7 metabolism remains to be determined. Nonetheless, this study demonstrates that there is a saturable endothelial mechanism of action of vitamin K2 (MK-7) that was achieved with a relatively low dose of vitamin K2 (MK-7) and low nanomolar range of plasma vitamin K2 concentration.

The mechanisms involved in vitamin K2-induced improvement of endothelial function was not determined in this study. However, this study confirms that the endothelial effects of vitamin K2 are independent of a coagulation system, as evidenced by unchanged thrombin activity measured based on CAT, a reference method for the quantitative assessment of thrombin generation. The study also excludes the possibility that the improvement of endothelial function by vitamin K2 demonstrated in ApoE/LDLR$^{-/-}$ mice was linked to the inhibition of atherosclerotic plaque formation, as vitamin K2 afforded vasoprotective effects independently of whether endothelial dysfunction was treated with vitamin K2 prior to or concurrently with the occurrence of atherosclerotic plaques in young and older ApoE/LDLR$^{-/-}$ mice.

In contrast to the lack of the anti-atherosclerotic effect, vitamin K2 provided a reduced media thickness similar in magnitude for low and high dose of vitamin K2, which could be linked to vitamin K2 dependent carboxylation of matrix Gla-protein (MGP) in smooth muscle cells, a well-described mechanisms of vitamin K2. Hence, s low dose of vitamin K2 was sufficient to improve carboxylation status in smooth muscle cells of the vascular wall in ApoE/LDLR$^{-/-}$ mice. Whether improvement of endothelial NO-dependent function was linked to improved carboxylation status in endothelium, to MGP, or to other vitamin K-dependent proteins (VKPDs) remains to be determined.

A number of VKPDs were identified in the endothelium, including MGP, an important inhibitor of vascular calcification, Gas6 involved in endothelial survival, and osteocalcin (OC). Based on this study, it is still undetermined which types of VKPDs play a role in the regulation of NO-dependent function. One possibility is that the beneficial effects of vitamin K2 on smooth muscle cells or the anti-inflammatory effects of vitamin K2 also contribute to the improved endothelial function induced by vitamin K2. Furthermore, VKDP-independent mechanisms in endothelium or other cells may also be a possibility.

In any event, the present study shows that a low dose of vitamin K2, i.e., compatible with effective vasoprotective doses in humans (180-360 µg), improved endothelial function. The data imply that the endothelial effects of vitamin K2 discovered here could contribute to the beneficial effects of vitamin K2 on vascular health. Furthermore, endothelial dysfunction could possibly also be involved in vitamin K insufficiency-associated cardiovascular mortality. This study provides evidence that vitamin K2 treatment improves endothelial dysfunction in ApoE/LDLR$^{-/-}$ mice, a genetically-driven model of high hypercholesterolemia that represent a distinct endothelial and vascular pathology as compared with aging or menopausal women, studied in human trials, which showed negative results of vitamin K2 treatment on endothelial function. Hence, a possible disease-specific effect of vitamin K2 treatment on endothelial function should be considered.

In conclusion, the effects of vitamin K2 on endothelial function shown by this study are surprising. Given the fact that the endothelium is involved in most, if not all, disease states (either as a primary determinant of pathophysiology or as a victim of collateral damage), vitamin K2 may be considered a potential vasoprotective agent in various diseases associated with endothelial dysfunction.

What is claimed is:

1. A method of increasing endothelial nitric oxide production in a human before development of atherosclerosis comprising:

determining a first nitrite plasma concentration in the human;

administering to the human an effective amount of vitamin K2 for a period of less than 4 weeks at an amount of 150 to 500 µg/day; and determining a second nitrite plasma concentration in the human after the period.

2. The method of claim 1, wherein the human suffers from hypercholesterolemia.

3. The method of claim 2, wherein the human suffers from hypercholesterolemia without atherosclerotic plaques.

4. The method of claim 1, wherein said vitamin K2 is menaquinone.

5. The method of claim 3, wherein said human is administered vitamin K2 in an amount of 180-360 µg/day.

6. The method of claim 1, wherein said human is administered vitamin K2 in an amount of 180-360 µg/day.

7. The method of claim 1, wherein said human is administered vitamin K2 in an amount of 200-500 µg/day.

8. The method of claim 1, wherein said human is administered vitamin K2 in an amount of 400-500 µg/day.

* * * * *

UNITED STATES PATENT AND TRADEMARK OFFICE
CERTIFICATE OF CORRECTION

| | | |
|---|---|---|
| PATENT NO. | : 11,911,349 B2 | Page 1 of 1 |
| APPLICATION NO. | : 16/372173 | |
| DATED | : February 27, 2024 | |
| INVENTOR(S) | : Stefan Chlopicki | |

It is certified that error appears in the above-identified patent and that said Letters Patent is hereby corrected as shown below:

On the Title Page

In Item (72) Inventors:
Please correct the city and country of the first and second inventor to read as follows:
-- Kraków, (PL) --

Signed and Sealed this
Second Day of April, 2024

Katherine Kelly Vidal
*Director of the United States Patent and Trademark Office*